(12) United States Patent
Boerjes et al.

(10) Patent No.: US 8,454,365 B2
(45) Date of Patent: Jun. 4, 2013

(54) DIGITAL DENTISTRY

(75) Inventors: Joseph Boerjes, Medford, MA (US); Simon K. J. Schiessl, Berlin (DE); Michael P. Girard, Ontario (CA); Micah J. Rosenbloom, Boston, MA (US); Eric B. Paley, Somerville, MA (US); Edward K. Tekeian, Cambridge, MA (US); Steven V. Weeks, North Andover, MA (US); David E. Altobelli, Hollis, NH (US); Douglas M. Johnston, Winchester, MA (US); Janos Rohaly, Acton, MA (US)

(73) Assignee: 3M Innovative Properties Company, Saint Paul, MN (US)

( * ) Notice: Subject to any disclaimer, the term of this patent is extended or adjusted under 35 U.S.C. 154(b) by 338 days.

(21) Appl. No.: 12/161,252

(22) PCT Filed: Jan. 19, 2007

(86) PCT No.: PCT/US2007/001547
§ 371 (c)(1),
(2), (4) Date: Jun. 2, 2009

(87) PCT Pub. No.: WO2007/084727
PCT Pub. Date: Jul. 26, 2007

(65) Prior Publication Data
US 2009/0298017 A1  Dec. 3, 2009

Related U.S. Application Data

(60) Provisional application No. 60/761,078, filed on Jan. 20, 2006.

(51) Int. Cl.
*A61C 5/00* (2006.01)

(52) U.S. Cl.
USPC .......................................... 433/223; 700/105

(58) Field of Classification Search
USPC ........... 433/223, 201.1, 202.1, 203.1; 700/97, 700/98, 105, 118, 163; 715/971
See application file for complete search history.

(56) References Cited

U.S. PATENT DOCUMENTS

| 4,265,619 A | 5/1981 | Lucki et al. |
| 4,270,901 A | 6/1981 | Comparetto |

(Continued)

FOREIGN PATENT DOCUMENTS

| DE | 19524855 | 1/1997 |
| DE | 10 2005 016 245 A1 | 10/2006 |

(Continued)

OTHER PUBLICATIONS

European Search Report, 62701EP008, PCT/US2007/001547, May 11, 2010.

(Continued)

*Primary Examiner* — Ralph Lewis

(57) ABSTRACT

The systems and methods disclosed herein employ a scanning system for capturing highly detailed digital dental models. These models may be used within a dentist's office for a wide array of dental functions including quality control, restoration design, and fitting. These models may also, or instead, be transmitted to dental laboratories that may, alone or in collaboration with the originating dentist or other dental professionals, transform the digital model into a physical realization of a dental hardware item.

13 Claims, 7 Drawing Sheets

U.S. PATENT DOCUMENTS

| | | | |
|---|---|---|---|
| 4,624,639 | A | 11/1986 | Wong |
| 4,846,684 | A | 7/1989 | Oestreich |
| 5,368,478 | A | 11/1994 | Andreiko et al. |
| 5,372,502 | A | 12/1994 | Massen et al. |
| 5,644,386 | A | 7/1997 | Jenkins et al. |
| 5,658,143 | A | 8/1997 | Kuperman |
| 5,740,222 | A | 4/1998 | Fujita et al. |
| 5,740,802 | A | 4/1998 | Nafis et al. |
| 5,771,310 | A | 6/1998 | Vannah |
| 5,999,840 | A | 12/1999 | Grimson et al. |
| 6,019,601 | A | 2/2000 | Cho |
| 6,044,232 | A | 3/2000 | Pan |
| 6,106,284 | A | 8/2000 | Cronin et al. |
| 6,141,105 | A | 10/2000 | Yahashi et al. |
| 6,201,889 | B1 | 3/2001 | Vannah |
| 6,247,927 | B1 | 6/2001 | Walter |
| 6,257,887 | B1 | 7/2001 | Heckerman et al. |
| 6,342,917 | B1 | 1/2002 | Amenta |
| 6,409,504 | B1 | 6/2002 | Jones et al. |
| 6,447,453 | B1 | 9/2002 | Roundhill et al. |
| 6,511,318 | B2 | 1/2003 | Kim |
| 6,512,838 | B1 | 1/2003 | Rafii et al. |
| 6,516,213 | B1 | 2/2003 | Nevo |
| 6,542,249 | B1 | 4/2003 | Kofman et al. |
| 6,545,637 | B1 | 4/2003 | Krull et al. |
| 6,575,751 | B1 * | 6/2003 | Lehmann et al. ............. 433/223 |
| 6,632,089 | B2 | 10/2003 | Rubbert et al. |
| 6,648,640 | B2 | 11/2003 | Rubbert et al. |
| 6,687,393 | B1 | 2/2004 | Skinner, Jr. |
| 6,738,063 | B2 | 5/2004 | Shen et al. |
| 6,775,404 | B1 | 8/2004 | Pagoulatos et al. |
| 6,786,726 | B2 * | 9/2004 | Lehmann et al. ............. 433/223 |
| 6,882,894 | B2 | 4/2005 | Durbin et al. |
| 6,957,118 | B2 | 10/2005 | Kopelman et al. |
| 6,976,627 | B1 | 12/2005 | Culp et al. |
| 6,996,261 | B2 | 2/2006 | deCharms |
| 7,010,150 | B1 | 3/2006 | Pfeiffer et al. |
| 7,063,532 | B1 | 6/2006 | Jones et al. |
| 7,428,481 | B2 | 9/2008 | Nikolskiy et al. |
| 7,474,932 | B2 * | 1/2009 | Geng ............................. 700/98 |
| 7,523,044 | B2 * | 4/2009 | Rosenblood ...................... 705/2 |
| 7,581,953 | B2 * | 9/2009 | Lehmann et al. ............. 433/223 |
| 7,819,662 | B2 | 10/2010 | Marshall et al. |
| 2002/0009380 | A1 | 1/2002 | Daskalon et al. |
| 2002/0031743 | A1 | 3/2002 | Kim |
| 2002/0115482 | A1 | 8/2002 | Taub |
| 2002/0119432 | A1 | 8/2002 | Ranta et al. |
| 2002/0180760 | A1 | 12/2002 | Rubbert et al. |
| 2003/0003420 | A1 | 1/2003 | Striezel |
| 2004/0029078 | A1 | 2/2004 | Marshall |
| 2004/0133293 | A1 | 7/2004 | Durbin et al. |
| 2004/0155975 | A1 | 8/2004 | Hart et al. |
| 2004/0179728 | A1 | 9/2004 | Littlefield et al. |
| 2004/0197727 | A1 | 10/2004 | Sachdeva et al. |
| 2004/0204787 | A1 | 10/2004 | Kopelman et al. |
| 2004/0220691 | A1 | 11/2004 | Hofmeister et al. |
| 2005/0070782 | A1 | 3/2005 | Brodkin |
| 2005/0089214 | A1 | 4/2005 | Rubbert et al. |
| 2005/0089822 | A1 | 4/2005 | Geng |
| 2005/0153255 | A1 | 7/2005 | Sporbert et al. |
| 2005/0153257 | A1 | 7/2005 | Durbin et al. |
| 2005/0170309 | A1 | 8/2005 | Raby et al. |
| 2005/0177261 | A1 | 8/2005 | Durbin et al. |
| 2005/0177266 | A1 | 8/2005 | Kopelman et al. |
| 2005/0186540 | A1 | 8/2005 | Taub et al. |
| 2005/0250075 | A1 | 11/2005 | Taub et al. |
| 2006/0003292 | A1 | 1/2006 | Lauren et al. |
| 2006/0093988 | A1 | 5/2006 | Swaelens et al. |
| 2006/0127858 | A1 | 6/2006 | Wen |
| 2006/0154198 | A1 | 7/2006 | Durbin et al. |
| 2006/0172261 | A1 * | 8/2006 | Garry ............................. 433/215 |
| 2007/0026363 | A1 * | 2/2007 | Lehmann et al. ............. 433/223 |
| 2007/0103460 | A1 | 5/2007 | Zhang et al. |
| 2008/0124681 | A1 | 5/2008 | Cha |
| 2008/0199829 | A1 | 8/2008 | Paley et al. |
| 2008/0233528 | A1 | 9/2008 | Kim et al. |

FOREIGN PATENT DOCUMENTS

| | | |
|---|---|---|
| EP | 1 650 529 A1 | 4/2006 |
| WO | WO 00/19929 | 4/2000 |
| WO | 2004/044787 A2 | 5/2004 |

OTHER PUBLICATIONS

European Search Report, 62701EP011, PCT/US2007/001652, May 11, 2010.

"Digital impressions: eliminating the weak link", *Lab Management Today* Jan. 2006, 20 et seq.

Ahmed et al., "3D Reconstruction of the Human Jaw from a Sequence of Images" Proceedings of the Comp. Vis. And Patt. Recog. (CVPR97) Conference, (1997) p. 1-8.

Ahmed et al., "Shape Recovery of the Jaw Impression from a Sequence of Images" Computer Vision and Image Processing Laboratory, University of Louisville, Department of Electrical Engineering, pp. 1-4.

Ares et al., "Position and Displacement Sensing with Shack-Hartmann wave-front sensors" Applied Opics, vol. 39, No. 10, (2000) pp. 1511-1520.

Blais, "Biris: A Simple 3-D Sensor" Electrical Engineering Division, SPIE vol. 728 Optics, Illumination, and Image Sensing for Machine Vision (1986) pp. 235-242.

Castellini, et al. "Hartmann Test Modification for Measuring Ophthalmic Progressive Lenses" Applied Optics, vol. 33, No. 19 (1994) pp. 4120-4124.

Hart, "High-Speed PIV Analysis Using Compressed Image Correlation" Massachusetts Institute of Technology, Journal of Fluids Engineering, vol. 120 (1998) pp. 463-470.

Hart, "PIV Error Correction" Experiments in Fluids 29 (2000) pp. 13-20.

Hart, "Super-Resolution PIV by Recursive Local-Correlation" Journal of Visualization, The Visualization Society of Japan, vol. 10 (1999) pp. 1-10.

Hassan et al., "A Complete Volumetric 3D Model of the Human Jaw" Computer Vision and Image Processing Lab, University of Louisville.

Hemayed et al., "Three Dimensional Model Building in Computer Vision with Orthodontic Application" TR-CVIP Nov. 1996, pp. 1-27.

Laude et al., "Hartmann wave-front scanner" Optics Letter, vol. 24, No. 24, (1999) pp. 1796-1798.

Motohashi et al., "A 3D Computer-Aided Design Systerm Applied to Diagnosis and Treatment Plannin in Orthodontics and Orthognathic Surgery" European Journal of Orthodontics 21 (1999) 263-274.

Schechner et al., "Depth from Defocus vs. Stereo: How Different Really Are They?" International Journal of Computer Vision, 39(2), (2000) pp. 141-162.

Tomasi et al., "Shape and Motion for Image Streams under Orthography: a Factorization Method" International Journal of Computer Vision, 9:2, (1992) pp. 137-154.

Yamany et al., "A 3D Reconstruction System for the Human Jam Using a Sequence of Optical Images" School of Dentistry, University of Louisville, pp. 1-22.

Yamany et al., "A System for Human Jaw Modeling Using Intra-Oral Images" Computer Vision and Image Processing Laboratory, p. 1-4.

Yamany et al., "Orthodontics Measurements using Computer Vision" Computer Vision and Image Processing Laboratory, University of Louisville, Department of Electrical Engineering, pp. 1-4.

* cited by examiner

DIGITAL DENTISTRY

CROSS REFERENCE TO RELATED APPLICATIONS

This application is a national stage filing under 35 U.S.C. 371 of PCT/US2007/001547, filed Jan. 19, 2007, which claims benefit of U.S. Provisional Application No. 60/761,078, filed Jan. 20, 2006, the disclosure of which is incorporated by reference in its entirety herein.

BACKGROUND

1. Field of the Invention

The invention relates to dentistry, and more particularly for dental applications of digital, three-dimensional representations of dentition.

2. Description of the Related Art

Dentistry today largely continues in the mold of the past, using techniques pioneered by ancient Egyptians. One basic technique for manufacturing a dental restoration, the so-called lost wax method, employs a wax pattern from which a metal casting is made. A mold of the wax pattern is made using a high-heat investment material. The mold is then heated in a furnace, the pattern is then burned out, and the investment ring is cast or filled with some type of alloy or some other substance to provide a final version of a dental restoration. A dentist bonds this prosthetic to a site in a patient's mouth that has been hand-prepared to match the prosthetic. As a significant disadvantage, a substantial burden is placed on practicing dentists to physically match restorations and tooth surfaces. Further complicating this process, the wax model itself is typically created from a physical cast of the patient's mouth. The casting process can introduce errors into a final restoration, as can material handling in the multiple steps carried out by a dental laboratory to go from the original dental impression to the final restoration.

In theory, digital dentistry offers manifest advantages of quality, portability, and durability as compared to cast models of physical impressions. However, advances in dentistry have been muted, at least in part due to the inability to easily capture adequate three-dimensional data for teeth and surrounding soft tissue. In addition, dentistry has achieved only limited gains from general improvements in manufacturing technologies because each dental patient and restoration presents a unique, one-off product.

There remains a need for dentistry tools that capture high-quality digital dental models, as well as tools that permit the design and manufacture of dental hardware from such models.

SUMMARY

The systems and methods disclosed herein employ a scanning system for capturing highly detailed digital dental models. These models may be used within a dentist's office for a wide array of dental functions including quality control, restoration design, and fitting. These models may also, or instead, be transmitted to dental laboratories that may, alone or in collaboration with the originating dentist or other dental professionals, transform the digital model into a physical realization of a dental hardware item.

A method disclosed herein includes acquiring a three-dimensional representation of one or more intraoral structures of a dental patient using an intraoral scanner; and providing the three-dimensional representation to a dental fabrication facility.

The method may further include fabricating a dental restoration at the dental fabrication facility using the three-dimensional representation. The dental fabrication facility may include a dental laboratory. The one or more intraoral structures may include at least one dental implant, at least one tooth, at least one tooth surface prepared for a dental restoration, at least one previously restored tooth, and/or at least one area of soft tissue. The method may further include fabricating a dental prosthesis at the dental fabrication facility using the three-dimensional representation.

The method may further include transmitting the three-dimensional representation to a dental laboratory and, in response, receiving an assessment of quality for the three-dimensional representation from the dental laboratory. The assessment of quality may be received before the dental patient leaves a dentist's office. The assessment of quality may include an assessment of acceptability of the three-dimensional representation. The method may further include transmitting the three-dimensional representation to a dental laboratory and, in response, receiving an assessment of quality of the at least one prepared tooth surface. Transmitting the three-dimensional representation to a dental fabrication facility may include transmitting to a remote dental laboratory for fabrication of a dental restoration for the one or more intraoral structures. The method may further include transmitting the three-dimensional representation to a dental data hub. The method may further include transmitting a prescription for the dental restoration with the three-dimensional representation. The method may further include transmitting the three-dimensional representation to a model production laboratory. The model production laboratory may be a milling facility, a manufacturing facility, or a three-dimensional rapid prototyping facility. Transmitting the three-dimensional representation to a dental fabrication facility may include providing the three-dimensional representation to an in-office dental laboratory for fabrication of a dental restoration for the one or more intraoral structures.

A computer program product disclosed herein includes computer executable code embodied in a computer readable medium that, when executed on one or more computer devices, may perform the steps of: acquiring one or more images of one or more intraoral structures of a dental patient from an intraoral scanner; converting the one or more images into a three-dimensional representation of the one or more intraoral structures; and transmitting the three-dimensional representation to a dental fabrication facility.

The computer program may further include computer code that performs the step of comparing quality of the three-dimensional representation to predefined quality criteria. The predefined quality criteria may include acceptability of the three-dimensional representation for fabrication. The computer program may further include computer code that performs the steps of: retrieving a prescription for at least one of a prosthesis or an appliance by a dentist; and combining the prescription with the three-dimensional representation prior to transmitting the three-dimensional representation. The one or more intraoral structures may include at least one dental implant, one tooth, or one tooth surface prepared for a dental restoration. The computer program may further include computer code that performs the step of comparing quality of the at least one prepared tooth surface to predefined quality criteria. The one or more intraoral structures may include at least one area of soft tissue.

A system disclosed herein includes an intraoral scanner for acquiring a three-dimensional representation of one or more intraoral structures of a dental patient; and a transmission means for transmitting the three-dimensional representation to a dental fabrication facility.

The system may further include a first fabrication means for fabricating a dental restoration at the dental fabrication facility using the three-dimensional representation. The one or more intraoral structures may include at least one dental implant, one tooth, least one tooth surface prepared for a dental restoration, or one area of soft tissue. The system may further include a second fabrication means for fabricating a dental prosthesis at the dental fabrication facility using the three-dimensional representation. The system may further include a quality assessment means for assessing quality of the three-dimensional representation. The quality assessment means may include a means for determining acceptability of the three-dimensional representation for use with the first fabrication means. The quality assessment means may include a means for determining acceptability of the three-dimensional representation for use with the second fabrication means. The one or more intraoral structures may include at least one tooth surface prepared for a dental restoration, wherein the quality assessment means includes a means for determining quality of the at least one prepared tooth surface.

In another aspect, a method disclosed herein includes receiving a three-dimensional representation of a tooth, the tooth prepared for a dental restoration; specifying a cementation void between the tooth surface and the dental restoration; and fabricating the dental restoration such that the dental restoration, when mated to the tooth surface, defines an empty space corresponding to the cementation void.

The method may include adjusting the cementation void, such as according to a dentist's preferences or according to the type of cement to be used in the cementation void. The cementation void may be specified by a dentist. The dentist may send the specification to a dental laboratory. The cementation void may be specified by a dental laboratory. The method may include three-dimensionally printing a die including the cementation void. The method may include fabricating a die including the cementation void with a stereo lithography apparatus. The method may include three-dimensionally printing a wax-up including the cementation void. The method may include milling a die including the cementation void. The method may include integrating the cementation void into a digital surface representation of the tooth. The method may include integrating the cementation void into a dental model. The three-dimensional representation may include a digital surface representation of the tooth. Fabricating the dental restoration may include fabricating the dental restoration in an in-house laboratory in a dentist's office. The method may further include fabricating an opposing arch for an arch including the tooth, the opposing arch including a die spacer having a predetermined thickness.

In another aspect, a computer program product disclosed herein includes computer executable code embodied in a computer readable medium that, when executed on one or more computer devices, performs the steps of: acquiring one or more images of a tooth of a dental patient from an intraoral scanner, the tooth including a tooth surface prepared for a dental restoration; converting the one or more images into a three-dimensional representation of the tooth; specifying a cementation void between the tooth surface and the dental restoration; combining the specification for the cementation void with the three-dimensional representation into a fabrication specification; and transmitting the fabrication specification to a dental fabrication facility.

A dentist may specify the cementation void. The computer program product may include code that performs the step of receiving a specification of the cementation void from the dental fabrication facility. The computer program product may include code for three-dimensionally printing the cementation void to a die. The computer program product may include code for three-dimensionally printing the cementation void to a wax up. The computer program product may include code that performs the step of integrating the cementation void into a digital surface representation of the tooth.

In another aspect, a system disclosed herein includes a first means for three-dimensionally representing a tooth, the tooth prepared for a dental restoration; a second means for specifying a cementation void, the cementation void representing an empty space between the tooth surface and the dental restoration; and a fabrication means for fabricating the dental restoration such that the dental restoration, when mated to the tooth surface, defines an empty space corresponding to the cementation void.

The system may include an adjustment means for adjusting the cementation void. The adjustment means may include means for incorporating a dentist's preferences. The adjustment means may include means for adjusting the cementation void according to a type of cement. The system may include a first printing means for three-dimensionally printing a die including the cementation void. The system may include a second printing means for three-dimensionally printing a wax-up including the cementation void. The system may include a milling means for milling a die including the cementation void. The system may include a milling means for milling an investment chamber for casting including the cementation void. The system may include a model means for integrating the cementation void into a model of a dental impression. The three-dimensional representation of a tooth may include a digital surface representation of the tooth.

In another aspect, a method disclosed herein includes fabricating a dental object; acquiring a first three-dimensional representation of the object; and measuring a dimensional accuracy of the first three-dimensional representation. The first three-dimensional representation may include a digital surface representation. The dental object may include a dental prosthesis, a dental implant, a dental appliance, a dental restoration, a restorative component, or an abutment. The method may include acquiring a second three-dimensional representation of one or more teeth including at least one tooth surface prepared for the dental object, wherein measuring a dimensional accuracy may include evaluating a fit between the item of the first three-dimensional representation and the at least one tooth surface of the second three-dimensional representation. The method may further include acquiring a second three-dimensional representation of one or more teeth including at least one tooth surface prepared for the dental object, wherein measuring a dimensional accuracy may include evaluating one or more contact points between the item of the first three-dimensional representation and the one or more teeth of the second three-dimensional representation when the item is virtually affixed to the at least one tooth surface. The method may further include acquiring a second three-dimensional representation of one or more teeth including at least one tooth surface prepared for the dental object and at least one opposing tooth, wherein measuring a dimensional accuracy may include evaluating one or more contact points between the item of the first three-dimensional representation and the at least one opposing tooth of the second three-dimensional representation when the item is virtually affixed to the at least one tooth surface. The second three-dimensional representation may be acquired as a plurality of separate scans. The second three-dimensional representation may be acquired as a continuous scan of the at least one tooth surface and the at least one opposing tooth in occlusion. A dentist may specify tightness of fit of the dental object. Measuring a dimensional accuracy may include quantifying tightness of fit of the dental object. Measuring a dimensional accuracy includes measuring quality of a margin.

A computer program product may include computer executable code embodied in a computer readable medium that, when executed on one or more computer devices, performs the steps of: acquiring one or more images of a dental object, converting the one or more images of the dental object into a first three-dimensional representation of the item; and measuring a dimensional accuracy of the first three-dimensional representation. The first three-dimensional representation may include a digital surface representation.

The dental object may include a dental prosthesis, a dental implant, a dental appliance, a dental restoration, a restorative component, or an abutment. The computer program product may include code that performs the steps of: acquiring one or more images of one or more teeth including at least one tooth surface prepared for the dental object; and converting the one or more images of the one or more teeth into a second three-dimensional representation of the one or more teeth, wherein measuring a dimensional accuracy includes evaluating a fit between the item of the first three-dimensional representation and the at least one tooth surface of the second three-dimensional representation. The computer program product may include code that performs the steps of: acquiring one or more images of one or more teeth including at least one tooth surface prepared for the dental object; converting the one or more images of the one or more teeth into a second three-dimensional representation of the one or more teeth; and generating one or more contact points between the item of the first three-dimensional representation and the one or more teeth of the second three-dimensional representation by virtually affixing the item to the at least one tooth surface, wherein measuring includes evaluating one or more contact points.

The computer program product may further include computer code that performs the steps of: acquiring one or more images of one or more teeth including at least one tooth surface prepared for the dental object and at least one opposing tooth; converting the one or more images of the one or more teeth and the at least one opposing tooth into a second three-dimensional representation of the one or more teeth and the at least one opposing tooth; and generating one or more contact points between the item of the first three-dimensional representation and the at least one opposing tooth of the second three-dimensional representation by virtually affixing the item to the at least one tooth surface, wherein measuring includes evaluating one or more contact points. Measuring a dimensional accuracy may include quantifying tightness of fit of the dental object. Measuring a dimensional accuracy may include measuring quality of a margin.

A system disclosed herein includes a fabrication means for fabricating a dental object; a first means for acquiring a first three-dimensional representation of the item; and a measurement means for measuring a dimensional accuracy of the first three-dimensional representation. The first three-dimensional representation may include a digital surface representation.

The dental object may include a dental prosthesis, a dental implant, a dental appliance, a dental restoration, a restorative component, or an abutment. The system may further include a second means for acquiring a second three-dimensional representation of one or more teeth including at least one tooth surface prepared for the dental object, wherein measuring a dimensional accuracy may include evaluating a fit between the item of the first three-dimensional representation and the at least one tooth surface of the second three-dimensional representation. The system may further include a second means for acquiring a second three-dimensional representation of one or more teeth including at least one tooth surface prepared for the dental object, wherein measuring a dimensional accuracy may include evaluating one or more contact points between the item of the first three-dimensional representation and the one or more teeth of the second three-dimensional representation when the item is virtually affixed to the at least one tooth surface. The system may further include a second means for acquiring a second three-dimensional representation of one or more teeth including at least one tooth surface prepared for the dental object and at least one opposing tooth, wherein measuring a dimensional accuracy may include evaluating one or more contact points between the item of the first three-dimensional representation and the at least one opposing tooth of the second three-dimensional representation when the item is virtually affixed to the at least one tooth surface. A dentist may specify tightness of fit of the dental object. Measuring a dimensional accuracy may include quantifying tightness of fit of the dental object. Measuring a dimensional accuracy includes measuring quality of a margin.

A method disclosed herein includes acquiring a three-dimensional representation including three-dimensional surface data for at least two independent dental structures; and acquiring motion data characterizing a relative motion of the at least two independent dental structures with respect to one another within a mouth.

The method may include deriving TMJ condyle paths of rotation and translation from the motion data and the three-dimensional surface data. The method may include providing input to a virtual dental articulator. The method may include providing specifications for a physical dental articulator. The method may include providing specifications for a disposable dental articulator. Acquiring the three-dimensional representation may include acquiring the three-dimensional representation using an intraoral scanner. Acquiring motion data may include acquiring motion data from a video source.

A computer program product disclosed herein includes computer executable code embodied in a computer readable medium that, when executed on one or more computer devices, may perform the steps of: acquiring one or more images of at least two independent dental structures of a dental patient from an intraoral scanner; converting the one or more images into a three-dimensional representation of the at least two independent dental structures; acquiring motion data characterizing a relative motion of the at least two independent dental structures with respect to one another; and combining the three-dimensional representation with the motion data to derive TMJ condyle paths of rotation and translation.

The computer program may include code that performs the steps of: generating an image sequence of the combined three-dimensional representation and the motion data; generating a display signal of the image sequence. Acquiring motion data may include acquiring motion data from a video source.

A system disclosed herein includes a first means for acquiring one or more images of at least two independent dental structures of a dental patient; a conversion means for converting the one or more images into a three-dimensional representation of the at least two independent dental structures; and a second means for acquiring motion data characterizing a relative motion of the at least two independent dental structures with respect to one another. The system may include an analysis means for deriving TMJ condyle paths of rotation and translation using the three-dimensional representation and the motion data.

The system may include an action means for combining the three-dimensional representation and the motion data to generate an articulation input. The system may include a first model means for virtually articulating the articulation input. The system may include a second model means for physically articulating the articulation input. The system may include a disposable model means for physically articulating the articulation input. The first means may include a means for acquiring the one or more images using an intraoral scanner. The second means may include a means for acquiring the motion data from a video source.

In another aspect, a method disclosed herein includes receiving an electronic dental prescription including prescription data, a first three-dimensional representation of one or more intraoral structures including at least one tooth surface prepared for an artificial dental object, and a second three-dimensional representation of the at least one tooth surface prior to preparation for the artificial dental object; and fabricating the artificial dental object for the one or more intraoral structures using the electronic dental prescription.

Receiving an electronic dental prescription may include receiving a three-dimensional representation from a dental data hub or from a dentist. Receiving a three-dimensional representation may include receiving a prescription for a dental restoration for the tooth surface. At least one of the first and second three-dimensional representations may include a digital surface representation of a full arch. The electronic dental prescription may include a prescription for an appliance, a prosthesis, or an item of dental hardware. Fabricating an artificial dental object may include fabricating a dental restoration in an in-house laboratory in a dentist's office.

A system disclosed herein includes a communication means for receiving a prescription data, a first three-dimensional representation of one or more intraoral structures including at least one tooth surface prepared for an artificial dental object, and a second three-dimensional representation of the at least one tooth surface prior to preparation for the artificial dental object; and a fabrication means for fabricating a dental restoration for the one or more intraoral structures using the three-dimensional representation.

The communication means may include a means for receiving the electronic dental prescription from a dental data hub or a dentist. The electronic dental prescription may include a prescription for a dental restoration. At least one of the first and second three-dimensional representations may include a digital surface representation of a full arch. The electronic dental prescription may include a prescription for one or more of an appliance, a prosthesis, and an item of dental hardware. The fabrication means may include in an in-house laboratory in a dentist's office.

In another aspect, a method disclosed herein includes a single dental visit, the steps of: acquiring a three-dimensional representation of one or more intraoral structures from a dental patient, the intraoral structures may include at least one tooth surface prepared for an artificial dental object; and processing the three-dimensional representation to provide feedback to a dentist concerning the at least one tooth surface.

The feedback may identify corrective action. The corrective action may include acquiring an additional three-dimensional representation of the one or more intraoral structures. The corrective action may include additional surface preparation of the at least one tooth. The feedback may identify a margin for fitting the dental restoration to the at least one tooth surface. The margin for fitting may be edited. The feedback may include a visual display of one or more regions of inadequate margin for fitting the dental restoration to the at least one tooth surface. The feedback may include a visual display recommending additional preparatory work required for the at least one tooth surface. The feedback may include a visual display recommending acquiring additional three-dimensional representations of one or more regions of the one or more intraoral structures. The feedback may include identifying an incomplete three-dimensional representation. The feedback may include identifying errors in the three-dimensional representation. The feedback may include visual highlighting of a margin line on a display of the three-dimensional representation.

A computer program product disclosed herein includes computer executable code embodied in a computer readable medium that, when executed on one or more computer devices, performs the steps of: acquiring one or more images of one or more intraoral structures of a dental patient, the intraoral structures including at least one tooth surface prepared for an artificial dental object; converting the one or more images into a three-dimensional representation of the one or more intraoral structures; analyzing the at least one tooth surface within the three-dimensional representation; generating a feedback signal, the feedback signal representative of the result of analyzing the at least one tooth surface; and outputting the feedback signal to provide feedback to a dentist.

The feedback signal may identify corrective action. The corrective action may include acquiring an additional one or more images of the one or more intraoral dental structures. The corrective action may include additional surface preparation of the at least one tooth. The feedback signal may identify a margin for fitting the dental restoration to the at least one tooth surface. The margin for fitting may be edited.

In another aspect, a system disclosed herein includes a scanning device configured to intraorally capture surface image data from a surface within a mouth of a dental patient; a computer coupled to the scanning device and receiving the surface image data therefrom, the computer configured to resolve the surface image data into a digital surface reconstruction, the computer further configured to generate a visualization of the digital surface reconstruction and provide the visualization as a display signal; and a display coupled to the computer and receiving the display signal therefrom, the display converting the display signal into a viewable image of the visualization. The surface may include dentition.

The scanning device may capture surface image data at a video frame rate. The system may include a user interface controlled by the computer and rendered on the display. The user interface may provide at least one tool for analyzing the surface. The user interface may include a tool that may provide real time feedback to the user. The real time feedback may include visual cues within the rendered image. The at least one tool may include a distance measurement tool, a tool that may evaluate adequacy of tooth structure removal from a dental restoration surface preparation, a tool that may evaluate adequacy of margin preparations, a tool that evaluates taper, a tool that evaluates undercut, or a tool that identifies scan deficiencies. The scan deficiencies may include holes in the surface. The at least one tool may include a tool that evaluates adequacy of removal path in multiple unit preparation. The at least one tool may include a tool that identifies irregularities in one or more occlusal surfaces requiring further preparation. Analyzing the surface may include an evaluation of suitability for three-dimensional printing, of suitability for milling, or of suitability for manual fabrication.

The computer may be further configured to automatically annotate the visualization with a visual indication of an evaluation. The visual indication includes an evaluation of contour of a surface preparation. The surface image data may include at least two tooth surfaces in occlusion. The visual indication may include an evaluation of margin of a surface preparation. The visual indication includes an evaluation of occlusal clearance of a surface preparation. The surface may include at least one surface prepared for a dental restoration, the evaluation including an evaluation of an adequacy of the at least one surface for receiving the dental restoration. The visual indication may include display of a contour of an actual tooth and a computer-generated surface preparation. The computer-generated surface preparation may be based upon intact configuration of the actual tooth prior to preparation.

In another aspect, a method disclosed herein includes receiving a three-dimensional representation that may include three-dimensional surface data from an intraoral structure including at least one tooth having a tooth surface prepared for a dental restoration; and presenting the three-dimensional representation in a user interface, the user interface may include a first tool for identifying a margin line for the dental restoration on the at least one tooth and a second tool for recessing a region of the three-dimensional representation below the margin line.

The first tool may provide automated identification of the margin line. The method may include removing a portion of the three-dimensional representation below the margin line with the second tool. The method may include removing a portion of the three-dimensional representation below the margin line with the second tool to provide a virtual ditched die, and three-dimensionally printing the ditched die.

A system disclosed herein includes a means for receiving a three-dimensional representation including three-dimensional surface data from an intraoral structure that may include at least one tooth having a tooth surface prepared for a dental restoration; and a user interface means for presenting the three-dimensional representation to a user, the user interface means may include a first tool means for identifying a margin line for the dental restoration on the at least one tooth and a second tool means for recessing a region of the three-dimensional representation below the margin line.

The first tool means may include a means for providing automated identification of the margin line. The system may include a means for removing a portion of the three-dimensional representation below the margin line. The system may include a means for removing a portion of the three-dimensional representation below the margin line to provide a virtual ditched die, and a means for three-dimensionally printing the ditched die.

In another aspect, a method disclosed herein includes acquiring a digital dental impression that may include three-dimensional surface data for at least two independent dental structures; and acquiring orientation data that may define a relative position of at least a portion of each of the at least two independent dental structures while in occlusion.

The orientation data may include three-dimensional surface data that spans the at least two independent dental structures while in occlusion. The orientation data may include three-dimensional surface data from each of the at least two independent dental structures while in occlusion. The occlusion may include a centric occlusion. The method may include applying the orientation data to position a virtual model of the at least two independent dental structures in a virtual articulator. The method may include fabricating models of each of the at least two independent dental structures and may apply the orientation data to position the models within a dental articulator. Acquiring orientation data may include acquiring three-dimensional data of a buccal side of dentition. Acquiring orientation data may include acquiring three-dimensional data of a labial side of dentition.

A system disclosed herein includes a first acquisition means for acquiring a digital dental impression including three-dimensional surface data for at least two independent dental structures; and a second acquisition means for that may acquire orientation data defining a relative position of at least a portion of each of the at least two independent dental structures while in occlusion.

The orientation data may include three-dimensional surface data that spans the at least two independent dental structures while in occlusion. The orientation data may include three-dimensional surface data from each of the at least two independent dental structures while in occlusion. The occlusion may include a centric occlusion. The system may include a model means for virtually articulating the at least two independent dental structures. The system may include a fabrication means for fabricating models of each of the at least two independent dental structures; and a model means for physically articulating the fabricated models. The orientation data may include three-dimensional data of a buccal side of dentition. The orientation data may include three-dimensional data of a labial side of dentition.

In another aspect, a method disclosed herein includes providing an intraoral three-dimensional scanning device; and scanning a plurality of teeth in an arch with the device in a scan path that may include a motion that begins at a first lingual point, traverses laterally over a first occlusal point and a first buccal point, translates to a second buccal point adjacent to the first buccal point, and then traverses laterally over a second occlusal point adjacent to the first occlusal point and a second lingual point adjacent to the first lingual point.

The method may include scanning the plurality of teeth in the arch with the device using a motion that translates to a third lingual point, and then may traverse laterally over a third occlusal point adjacent to the second occlusal point and a third buccal point adjacent to the second buccal point. The first lingual point and the second lingual point may be spaced apart such that a field of view of the scanning device includes at least one overlapping portion of the plurality of teeth when the scanning device is positioned to image the first and second lingual points respectively. The scan path may begin at a third buccal point, a third palatal point, or a third labial point.

In another aspect, a method disclosed herein includes within a single dental visit, the steps of: acquiring a three-dimensional representation of one or more intraoral structures including at least one tooth prepared for a dental restoration; and processing the three-dimensional representation that may provide feedback to a dentist concerning the at least one tooth.

The feedback may include a physical dimension, a dimension of the at least one tooth prior to preparation for the dental restoration, a contour of the at least one tooth, a clearance relative to one or more adjacent teeth for a dental restoration associated with the at least one tooth, or a position of the at least one tooth. The feedback may include a clearance relative to one or more teeth in an opposing occluded arch.

A computer program product disclosed herein includes computer executable code embodied in a computer readable medium that, when executed on one or more computer devices, performs the steps of: acquiring a three-dimensional representation of one or more intraoral structures that may include at least one tooth prepared for a dental restoration;

analyzing the three-dimensional representation; generating a feedback signal, the feedback signal may represent the analysis of the three-dimensional representation; and outputting the feedback signal to a dentist.

The feedback signal may include a physical dimension, a dimension of the at least one tooth prior to preparation for the dental restoration, a contour of the at least one tooth, a clearance relative to one or more adjacent teeth for a dental restoration associated with the at least one tooth, or a position of the at least one tooth. The feedback may include a clearance relative to one or more teeth in an opposing occluded arch.

A system disclosed herein includes an acquisition means for acquiring a three-dimensional representation of one or more intraoral structures including at least one tooth prepared for a dental restoration; an analysis means for analyzing the three-dimensional representation; a means for generating a feedback signal, the feedback signal representing the analysis of the three-dimensional representation; and a signal means for providing the feedback signal to a dentist.

The feedback signal may include a physical dimension, a dimension of the at least one tooth prior to preparation for the dental restoration, a contour of the at least one tooth, a clearance relative to one or more adjacent teeth for a dental restoration associated with the at least one tooth, or a position of the at least one tooth. The feedback may include a clearance relative to one or more teeth in an opposing occluded arch.

In another aspect, a method disclosed herein includes acquiring a three-dimensional representation from a dental patient including a digital surface representation of one or more intraoral structures; and providing a visual display of the three-dimensional representation in real time. The visual display of the three-dimensional representation may be superimposed on a real time two-dimensional video image of the one or more intraoral structures.

The one or more intraoral structures may include at least one tooth, at least one tooth surface prepared for a dental restoration, at least one restored tooth, at least one implant, or at least one area of soft tissue. The method may include processing the three-dimensional representation to generate user feedback concerning the one or more intraoral structures, and may provide a visual display of the user feedback. The feedback may include highlighting areas in the three-dimensional representation requiring additional attention.

A computer program product disclosed herein includes computer executable code embodied in a computer readable medium that, when executed on one or more computer devices, performs the steps of: acquiring one or more images of one or more intraoral structures; processing the one or more images into a three-dimensional representation including a digital surface representation of the one or more intraoral structures; and generating a first visual display signal of the three-dimensional representation in real time.

The computer program product may include computer code that performs the step of generating a second visual display signal wherein the three-dimensional representation is superimposed on a real time two-dimensional video image of the one or more intraoral structures. The one or more intraoral structures may include at least one tooth, at least one tooth surface prepared for a dental restoration, at least one restored tooth, at least one implant, or at least one area of soft tissue. The computer program product may include computer code that performs the steps of: analyzing the three-dimensional representation; may generate a feedback signal representative of the analysis of the three-dimensional representation; generate a third visual display signal including the feedback signal. The third visual display signal may include highlighted areas of the three-dimensional representation requiring additional attention.

A system disclosed herein includes: an acquisition means for acquiring a three-dimensional representation from a dental patient, the three-dimensional representation may include a digital surface representation of one or more intraoral structures; and a display means for visually displaying the three-dimensional representation in real time.

The display means may include a means for superimposing the three-dimensional representation on a real time two-dimensional video image of the one or more intraoral structures. The one or more intraoral structures may include at least one tooth, at least one tooth surface prepared for a dental restoration, at least one restored tooth, at least one implant, or at least one area of soft tissue. The system may include: an analysis means for analyzing the three-dimensional representation; a feedback means for generating a feedback signal representative of the analysis of the three-dimensional representation, wherein the display means includes a means for visually displaying the feedback signal. The feedback means may include a means for highlighting areas in the three-dimensional representation requiring additional attention.

In another aspect, a handheld imaging device for a three-dimensional imaging system disclosed herein includes: an elongated body including a first end, a second end, and a central axis; a video rate three-dimensional scanning device within the elongated body, the video rate three-dimensional scanning device may have an optical axis for receiving images, the optical axis substantially perpendicular to the central axis at a position near the first end of the elongated body; and the second end adapted for gripping by a human hand, and the second end may include a user input responsive to user manipulation to generate control signals for transmission to a processor associated with the imaging system. The user input may include a mouse, track ball, button, switch, mini joystick, touchpad, keypad, or thumb wheel. The control signals may be transmitted to the processor through a wireless communication medium. The user input may control a user interface associated with the imaging system.

A handheld imaging device for a three-dimensional imaging system disclosed herein includes: an elongated body including a central axis, a first end, and a second end, the second end adapted for gripping by a human hand and a central axis; a video rate three-dimensional scanning device within the elongated body, the video rate three-dimensional scanning device having an optical axis for receiving images, the optical axis substantially perpendicular to the central axis at a position near the first end of the elongated body; and a physical offset shaped and sized to maintain a desired distance of the first end from an imaging subject along the optical axis. The physical offset may include one or more wheels for slidably engaging a surface of the imaging subject.

In another aspect, a method disclosed herein includes: acquiring a three-dimensional representation from a dental patient including a digital surface representation of one or more intraoral structures, the intraoral structures may include a dental arch; processing the three-dimensional representation that may provide a digital dental model including one or more alignment guides to aid in positioning an orthodontic fixture; and fabricating a physical model from the digital dental model.

The method may include constructing the orthodontic fixture on the physical model using the alignment guides. The method may include constructing a support for the orthodontic fixture on the digital dental model. The alignment guides may include visual markings. The alignment guides may include at least one substantially horizontal shelf for the orthodontic fixture. Processing may include virtually placing a plurality of orthodontic brackets onto the three-dimensional representation, and adding a plurality of bracket supports to the digital dental model to support a physical realization of the plurality of orthodontic brackets on the physical model. The method may include fabricating the physical realization of the plurality of orthodontic brackets, positioning each one of the plurality of orthodontic brackets onto the physical model, and vacuum forming an appliance over the plurality of orthodontic brackets, the appliance maintaining the plurality of orthodontic brackets in fixed relation to one another. The method may include applying the appliance with the plurality of orthodontic brackets to the dental arch. The appliance may be formed of a soft, clear material. The method may include transmitting the digital dental model to a remote dental laboratory. Processing may include virtually placing a plurality of orthodontic brackets onto the three-dimensional representation in a bracket arrangement, and generating a digital model of a bracket guide adapted to position a physical realization of the plurality of orthodontic brackets in the bracket arrangement on the dental arch. The method may include three-dimensionally printing the bracket guide. The physical model may include fabricating the physical model in an in-house dental laboratory in a dentist's office.

In another aspect, a method disclosed herein includes: acquiring a three-dimensional representation from a dental patient including a digital surface representation of one or more intraoral structures, the intraoral structures may include a dental arch; adding a plurality of virtual brackets to the three-dimensional representation to provide a bracket model; processing the bracket model to generate a bracket guide model, the bracket guide model adapted to maintain a physical realization of the plurality of virtual brackets in a fixed orientation with respect to one another, the fixed orientation corresponding to a desired orientation of the physical realization on the dental arch; fabricating a bracket guide from the bracket guide model; and attaching the physical realization of the plurality of virtual brackets to the bracket guide model.

A computer program product disclosed herein includes computer executable code embodied in a computer readable medium that, when executed on one or more computer devices, performs the steps of: acquiring one or more images of one or more intraoral structures, the intraoral structures may include a dental arch; processing the one or more images into a three-dimensional representation of the one or more intraoral structures; transforming the three-dimensional representation into a digital dental model, the digital dental model including one or more orthodontic fixture alignment guides; and generating a virtual orthodontic fixture using the alignment guides.

The computer program product may include code that performs the step of constructing a support for the virtual orthodontic fixture on the digital dental model. The alignment guides may include visual markings. The alignment guides may include at least one substantially horizontal shelf for the virtual orthodontic fixture. Transforming may include virtually placing a plurality of orthodontic brackets onto the dental arch of the three-dimensional representation, and adding a plurality of bracket supports to the digital dental model. The computer program product may include code that performs the step of transmitting the digital dental model to a remote dental laboratory.

A system disclosed herein includes: an acquisition means for acquiring a three-dimensional representation from a dental patient including a digital surface representation of one or more intraoral structures, the intraoral structures may include a dental arch; a processing means for processing the three-dimensional representation that may provide a digital dental model including one or more alignment guides to aid in positioning an orthodontic fixture; and a first fabrication means for fabricating a physical model from the digital dental model.

The system may include a means for constructing the orthodontic fixture on the physical model using the alignment guides. The processing means may include a means for constructing a support for the orthodontic fixture on the digital dental model. The alignment guides may include visual markings. The alignment guides may include at least one substantially horizontal shelf for the orthodontic fixture. The processing means may include a means for virtually placing a plurality of orthodontic brackets onto the three-dimensional representation, and adding a plurality of bracket supports to the digital dental model to support a physical realization of the plurality of orthodontic brackets on the physical model. The system may include a second fabrication means for fabricating the physical realization of the plurality of orthodontic brackets, a positioning means for positioning each one of the plurality of orthodontic brackets onto the physical model, and a forming means for vacuum forming an appliance over the plurality of orthodontic brackets, the appliance maintaining the plurality of orthodontic brackets in fixed relation to one another. The system may include a means for applying the appliance with the plurality of orthodontic brackets to the dental arch. The appliance may be formed of a soft, clear material. The system may include a communication means for transmitting the digital dental model to a remote dental laboratory. The processing means may include a means for virtually placing a plurality of orthodontic brackets onto the three-dimensional representation in a bracket arrangement, and a model means for generating a digital model of a bracket guide adapted to position a physical realization of the plurality of orthodontic brackets in the bracket arrangement on the dental arch. The system may include a printing means for three-dimensionally printing the bracket guide. The fabrication means may include a means for fabricating the physical model in an in-house dental laboratory in a dentist's office.

A three-dimensional data acquisition system adapted for intraoral acquisition of dental data from one or more intraoral structures, as disclosed herein, may include a first operating mode for capturing scan data and rendering a low-quality three-dimensional image from the scan data in real time, and a second operating mode for generating a high-quality three dimensional image from the scan data after exiting the first operating mode, the high-quality three-dimensional image may have greater spatial resolution than the low-quality three-dimensional image.

The system may further including a display that renders the low-quality three-dimensional image superimposed on a video image of the one or more intraoral structures. Rendering a low-quality three-dimensional image may include rendering the low-quality three-dimensional image at a frame rate of the video image. The system may include a communications interface for transmitting the high-quality three-dimensional image to a dental laboratory.

In another aspect, a system disclosed herein includes: a scanning device configured to intraorally capture surface image data from a surface within a mouth of a dental patient; a computer coupled to the scanning device and receiving the surface image data therefrom, the computer configured to resolve the surface image data into a three-dimensional representation, the computer may be further configured to generate a visualization of the three-dimensional representation and to provide the visualization as a display signal; and a display coupled to the computer and receiving the display signal therefrom, the display adapted to convert the display signal into a viewable image, the display being a touch-screen display adapted to receive a user input through direct contact with a surface of the display, wherein the user input is interpreted by the computer to affect manipulation of the three-dimensional representation. The user input may affect rotational orientation of the visualization on the display.

The display may include areas for one or more user controls accessible through the touch-screen display. The user controls may include a zoom control, a pan control, or case management controls. The case management controls may include a control to transmit the three-dimensional representation to a dental lab, a control to evaluate quality of the three-dimensional representation, a tool to edit the three-dimensional representation, or a control to create a dental prescription.

The user controls may include a control to define a cementation void, a control to define a margin line, a control to infer a margin line from the three-dimensional representation, a control to recess a region of the three-dimensional representation below a margin line, a control to virtually fit a dental restoration to a prepared tooth surface, include a virtual dental articulator, or include a tool to design a dental restoration fitted to the surface within the mouth of the dental patient.

The three-dimensional model may include two arches; the display may include an area for one or more user controls accessible through the touch-screen display to permit positioning the two arches within a virtual articulator. The system may include a user interface displayed on the display and controlled by the computer. The user interface may be accessible through the touch-screen.

A system disclosed herein includes: a digital dental impression that may include three-dimensional digital surface data for one or more intraoral structures, the digital dental impression may be captured using a three-dimensional intraoral scanning device and stored in a computer readable medium; a first computer may be configured to render the digital dental impression from a point of view; and a second computer at a remote location may be configure to simultaneously render the digital dental impression from the point of view.

The system may include a control for passing control of the point of view between the first computer and the second computer. The system may include the first computer and the second computer including a collaborative tool for manipulating the model, for sectioning the model, or for rearranging one or more sections of the model. The system may include the first computer and the second computer including a collaborative cursor control tool. The system may include the first computer and the second computer connected by a communication channel. The communication channel may include one or more of VoIP, IRC, video conferencing, or instant messaging. The second computer may be operated by a consulting dentist, a dental technician, in a dental laboratory, or by an oral surgeon. The second computer may be operated by a dental specialist including one or more of a periodontist, a prosthodontist, a pedodontist, an orthodontic specialist, an oral and maxillofacial surgery specialist, an oral and maxillofacial radiology specialist, an endodontist, and an oral and maxillofacial pathologist.

A method disclosed herein includes: seating a dental patient in a clinical office; acquiring a digital dental impression that may include three-dimensional digital surface data for one or more intraoral structures from an intraoral scan of the dental patient; transmitting the digital dental impression to a dental laboratory before the patient leaves the office; receiving an evaluation of the digital dental impression from the dental laboratory before the patient leaves the office; and if the evaluation is unfavorable, repeating the step of acquiring the digital dental impression.

If the evaluation includes an identification of at least one region of the one or more intraoral structures requiring additional preparation, the method may include preparing the one or more intraoral structures according to the evaluation. The evaluation may include an evaluation of surface continuity, an evaluation of data density, or an evaluation of feature detail. The one or more intraoral structures may include a tooth surface prepared for a dental restoration. The digital dental impression may include a case plan for the restoration. The case plan may include a type of restoration, a design of restoration, or a list of restoration components. The list of restoration components may include a full ceramic component. The list of restoration components may include a PFM component. The case plan may include a specification of one or more restoration materials.

A system disclosed herein includes: a means for acquiring a digital dental impression, the digital dental impression may include three-dimensional digital surface data for one or more intraoral structures from an intraoral scan of a dental patient seated in a clinical office; a request means for transmitting the digital dental impression to a dental laboratory before the patient leaves the office; an evaluation means for determining if the digital dental impression must be reacquired before the patient leaves the office; and a response means for transmitting the determination to the clinical office.

The evaluation means may include a means for evaluating surface continuity, a means for evaluating data density, or a means for evaluating feature detail. The one or more intraoral structures may include a tooth surface prepared for a dental restoration. The digital dental impression may include a case plan for the restoration, a type of restoration, a design of restoration, or a list of restoration components. The list of restoration components may include a full ceramic component. The list of restoration components may include a PFM component. The case plan may include a specification of one or more restoration materials.

A system disclosed herein includes: a scanning device for real time capture of three-dimensional surface data; a monitor that may render the three-dimensional surface data in real time; a processor that may be configure to evaluate quality of the three-dimensional surface data, and may generate a signal representative of a data quality during a scan; and a feedback device that may be responsive to the signal to produce a user alert concerning the data quality when the data quality degrades below a predetermined threshold.

The scanning device may resolve the three-dimensional surface data from a plurality of two-dimensional image sets, and wherein the evaluation of quality may include evaluation of ability to determine spatial relationships from the plurality of two-dimensional image sets. The evaluation of quality may include evaluation of point cloud density. The evaluation of quality may include evaluation of scanning device motion. The feedback device may include an LED, a speaker, a buzzer, a vibrator, or a wand. The feedback device may be positioned on the wand. The feedback device may be further responsive to the signal to produce a second user alert when the data quality is within an acceptable range.

In another aspect, a method disclosed in herein may include: scheduling a preparation visit for a dental restoration for a patient; obtaining a digital surface representation of one or more intraoral structures of the patient, this may include at least one tooth associated with the dental restoration; and fabricating a temporary restoration based upon the digital surface representation.

Fabricating a temporary restoration may include transmitting the digital surface representation to a dental laboratory. Fabricating a temporary restoration may include applying the digital surface representation to prepare a design for the temporary restoration and transmitting the design to a dental laboratory. The method may include three-dimensionally printing the temporary restoration. The method may include three-dimensionally printing the temporary restoration at a dentist's office where the preparation visit is scheduled. The method may include milling the temporary restoration. The method may include milling the temporary restoration at a dental office where the preparation visit is scheduled. Obtaining a digital surface representation may include three-dimensionally scanning the one or more intraoral structures on a day of the preparation visit. Obtaining a digital surface representation may include retrieving the digital surface representation from prior dental data for the patient. Fabricating the temporary restoration may include fabricating the temporary restoration prior to the preparation visit, the temporary restoration may include one or more characteristics of the at least one tooth. The method may include, on the day of the preparation visit, adapting a surface of the at least one tooth to receive the temporary restoration. The method may include, on the day of the preparation visit, adapting the temporary restoration to fit a prepared surface of the at least one tooth. The step of fabricating may be performed at an in-house dental laboratory at a dentist's office.

A method disclosed herein includes: acquiring a digital dental impression including three-dimensional digital surface data for one or more intraoral structures, the intraoral structures may include at least one tooth surface prepared for a dental restoration; and acquiring additional three-dimensional data with greater spatial resolution around the at least one tooth surface prepared for the dental restoration.

The acquiring additional three-dimensional data may include acquiring additional data from the at least one tooth surface, post-processing source data for the digital dental impression, or post-processing the three-dimensional digital surface data.

A computer program product disclosed herein includes computer executable code embodied in a computer readable medium that, when executed on one or more computer devices, may perform the steps of: acquiring one or more images of one or more intraoral structures, the intraoral structures may include at least one tooth surface prepared for a dental restoration; and generating a digital dental impression that may include three-dimensional digital surface data from the one or more images.

The computer program product may include code that performs the step of post-processing source data for the digital dental impression to generate additional three-dimensional data with greater spatial resolution. The computer program product may include code that performs the step of post-processing the three-dimensional digital surface data to generate additional three-dimensional data with greater spatial resolution.

A system disclosed herein includes: a first means for acquiring a digital dental impression that may include three-dimensional digital surface data for one or more intraoral structures, the intraoral structures may include at least one tooth surface prepared for a dental restoration; and a second means for acquiring additional three-dimensional data with greater spatial resolution around the at least one tooth surface prepared for the dental restoration.

The second means may include a means for acquiring additional data from the at least one tooth surface, a means for post-processing source data for the digital dental impression, or a means for post-processing the three-dimensional digital surface data.

A method disclosed herein includes: acquiring a digital surface representation for one or more intraoral structures, the intraoral structures may include at least one tooth surface prepared for a dental restoration; fabricating a kit from the digital surface representation, the kit may include two or more components suitable for use in fabrication of the dental restoration; and sending the kit to a dental laboratory for fabrication of the dental restoration. The kit may include one or more of a die, a quad model, an opposing quad model, an opposing model, a base, a pre-articulated base, and a waxup.

The method may include transmitting the digital surface representation to a production facility. The step of fabricating may be performed at the production facility. The kit may include one or more components selected from the group of pre-cut components, pre-indexed components, and pre-articulated components. The step of fabricating may be performed at a dentist's office.

An artificial dental object disclosed herein includes an exposed surface, the exposed surface finished with a texture to enhance acquisition of three dimensional image data from the exposed surface with a multi-aperture three-dimensional scanning device. The texture may include pseudo-random three-dimensional noise.

The artificial dental object may include an impression coping, a fixture, a healing abutment, or a temporary impression coping. The artificial dental object may include a dental prosthesis, a dental restoration, a dental appliance, or an item of dental hardware.

In another aspect, a method disclosed herein includes acquiring a three-dimensional representation of one or more intraoral structures, the intraoral structures including at least one intraoral surface suitable for an artificial dental object; transmitting the three-dimensional representation to a dental insurer; and receiving authorization from the dental insurer to perform a dental procedure including the artificial dental object.

The artificial dental object may include one or more of an implant, a crown, an impression coping, a bridge, a fixture, and an abutment. The intraoral surface may include at least one edentulous space. The intraoral surface may include at least one tooth surface.

A computer program product disclosed herein may include code that, when executed on one or more computer devices, performs the steps of: acquiring a three-dimensional representation of one or more intraoral structures, the intraoral structures including at least one intraoral surface suitable for an artificial dental object; transmitting the three-dimensional representation to a dental insurer; and receiving authorization from the dental insurer to perform a dental procedure including the artificial dental object.

The artificial dental object may include one or more of an implant, a crown, an impression coping, a fixture, a bridge, and an abutment. The intraoral surface may include at least one edentulous space. The intraoral surface may include at least one tooth surface.

A system disclosed herein includes a means for acquiring a three-dimensional representation of one or more intraoral structures, the intraoral structures including at least one intraoral surface suitable for an artificial dental object; a first communication means for transmitting the three-dimensional representation to a dental insurer; and a second communication means for receiving authorization from the dental insurer to perform a dental procedure including the artificial dental object.

The artificial dental object may include one or more of an implant, a crown, an impression coping, a fixture, a bridge and an abutment. The at least one intraoral surface may include an edentulous space. The at least one intraoral surface includes a tooth surface.

In another aspect, a method disclosed herein includes acquiring a three-dimensional representation of one or more intraoral structures, the intraoral structures including at least one intraoral surface related to a dental procedure; and transmitting the three-dimensional representation to a dental insurer as a record of the dental procedure.

The dental procedure may relate to one or more of an implant, a crown, an impression coping, a fixture, a bridge, and an abutment. The method may include receiving a payment from the insurer for a procedure involving the artificial dental object. The intraoral surface may include an edentulous space. The intraoral surface may include a tooth surface prepared for an artificial dental object. The intraoral surface may include a restored tooth.

A computer program product disclosed herein includes computer executable code embodied in a computer readable medium that, when executed on one or more computer devices, performs the steps of: acquiring a three-dimensional representation of one or more intraoral structures, the intraoral structures including at one intraoral surface related to a dental procedure; and transmitting the three-dimensional representation to a dental insurer as a record of the dental procedure.

The dental procedure may relate to one or more of an implant, a crown, an impression coping, a bridge, and an abutment. The code may further include code that performs the step of receiving a record of payment from the insurer for the dental procedure. The intraoral surface may include an edentulous space. The intraoral surface may include a tooth surface prepared for an artificial dental object. The intraoral surface may include a restored tooth.

A system disclosed herein may include a means for acquiring a three-dimensional representation of one or more intraoral structures, the intraoral structures including at least one intraoral surface related to a dental procedure; and a communication means for transmitting the three-dimensional representation to a dental insurer as a record of the dental procedure.

The dental procedure may to one or more of an implant, a crown, an impression coping, a bridge, and an abutment. The communication means may include a means for receiving a payment from the insurer for the dental procedure.

In another aspect, a method disclosed herein includes receiving a three-dimensional representation of one or more intraoral structures from a dentist; receiving a proposed dental procedure from the dentist; determining whether the proposed dental procedure is appropriate for the one or more intraoral structures; and transmitting a reply to the dentist. The reply may include an approval to perform the dental procedure. The reply may include a denial to perform the dental procedure. The method may include authorizing payment for the dental procedure.

A computer program product disclosed herein includes computer executable code embodied in a computer readable medium that, when executed on one or more computer devices, may perform the steps of: receiving a three-dimensional representation of one or more intraoral structures from a dentist; receiving a proposed dental procedure from the dentist; comparing the proposed dental procedure to a predetermined list of appropriate procedures for the one or more intraoral structures; and transmitting a reply to the dentist. The reply may include an approval to perform the dental procedure. The reply may include a denial to perform the dental procedure. The computer program product may include computer code that performs the step of authorizing payment for the dental procedure.

A system disclosed herein includes: a first means for receiving a three-dimensional representation of one or more intraoral structures from a dentist; a second means for receiving a proposed dental procedure from the dentist; an evaluation means for determining whether the proposed dental procedure is appropriate for the one or more intraoral structures; and a reply means for transmitting a reply to the dentist. The reply may include an approval to perform the dental procedure. The reply may include a denial to perform the dental procedure. The system may include a means for authorizing payment for the dental procedure.

A system disclosed herein includes: a dental data repository coupled to a communications network, the dental data repository may be adapted to receive dental data including three-dimensional representations of intraoral structures and prescriptions for dental procedures from a plurality of dentists.

The dental data repository may be adapted to transmit prescriptions and three-dimensional representations to a plurality of dental laboratories. The at least one of the prescriptions may identify a specific one of the plurality of dental laboratories. The dental data repository may be further adapted to communicate with one or more dental insurers for authorization of dental procedures. The dental data repository may be further adapted to communicate with one or more dental insurers to coordinate payment for dental procedures. The system may include a dental laboratory interface for the plurality of dental laboratories to provide status on work in progress. The system may include a dental laboratory interface for the plurality of dental laboratories to receive work assignments. The system may include a dentist interface for the plurality of dentists to monitor work in progress. The system may include a dentist interface for the plurality of dentists to submit prescriptions and three-dimensional representations. The system may include a transaction engine for transmitting payments among two or more of one of the plurality of dentists, one of the plurality of dental laboratories, and one of the one or more dental insurers. The system may include a collaboration interface for two or more of the plurality of dentists to collaborate on a dental matter.

BRIEF DESCRIPTION OF THE FIGURES

The invention and the following detailed description of certain embodiments thereof may be understood by reference to the following figures.

DETAILED DESCRIPTION

Figure 1:
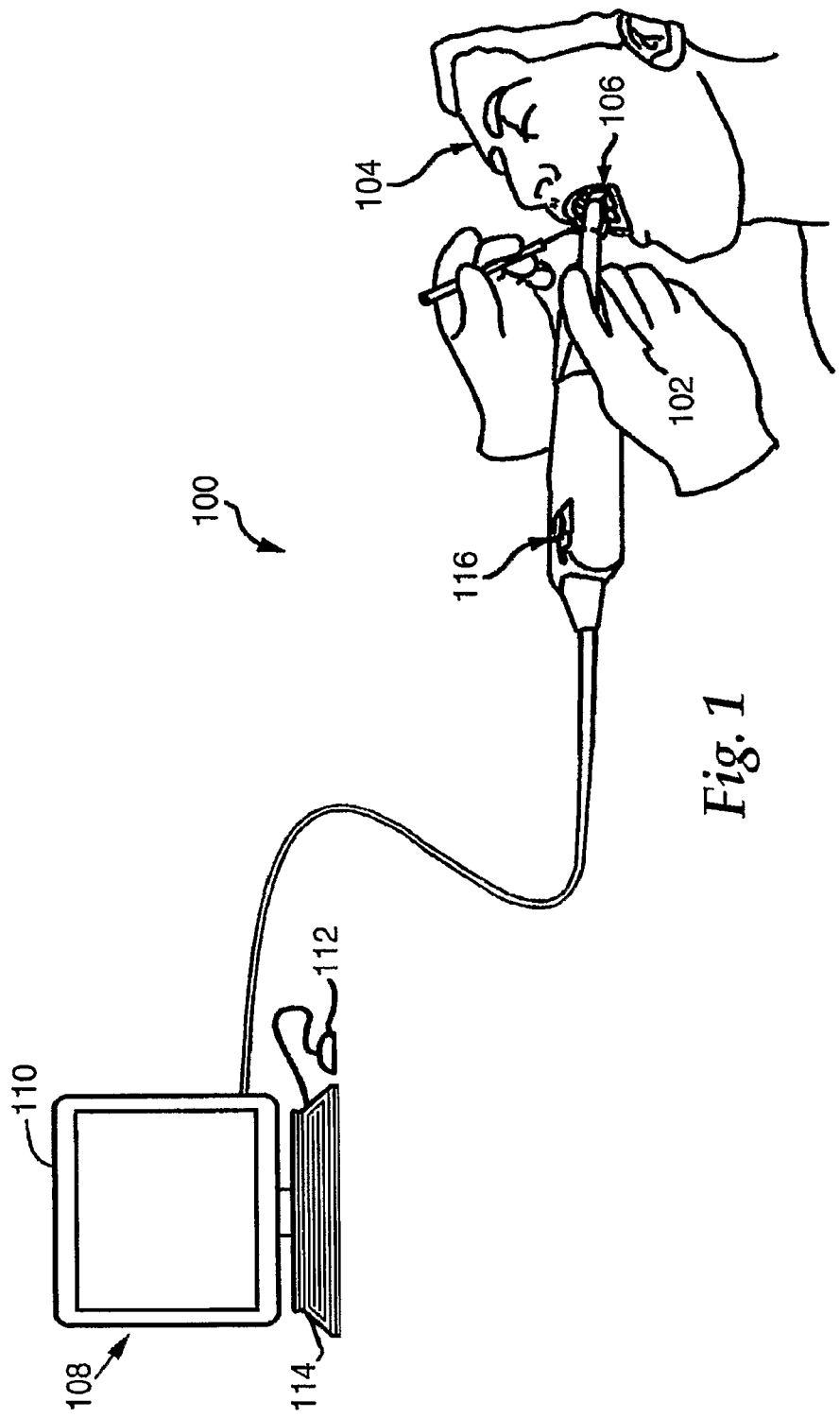
FIG. 1 shows a dental image capture system.

Described are a wide array of systems and methods for digital dentistry. However, it will be appreciated that the inventive concepts disclosed herein are not limited to the specific embodiments disclosed. For example, the general techniques disclosed herein may be usefully employed in any environment where precise, three-dimensional data might be usefully captured and processed, including orthopedics, digital animation, and customized manufacturing. In addition, while numerous variations and implementations of digital dentistry techniques are described, it will be appreciated that other combinations of the specific scanning, processing, and manufacturing techniques described herein may be used, and that such variations are intended to fall within the scope of this disclosure.

In the following description, the term "image" generally refers to a two-dimensional set of pixels forming a two-dimensional view of a subject within an image plane. The term "image set" generally refers to a set of related two dimensional images that might be resolved into three-dimensional data. The term "point cloud" generally refers to a three-dimensional set of points forming a three-dimensional view of the subject reconstructed from a number of two-dimensional views. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

The terms "three-dimensional surface representation", "digital surface representation", "three-dimensional surface map", and the like, as used herein, are intended to refer to any three-dimensional surface map of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context.

A "three-dimensional representation" may include any of the three-dimensional surface representations described above, as well as volumetric and other representations, unless a different meaning is explicitly provided or otherwise clear from the context.

In general, the terms "render" or "rendering" refer to a two-dimensional visualization of a three-dimensional object, such as for display on a monitor. However, it will be understood that three-dimensional rendering technologies exist, and may be usefully employed with the systems and methods disclosed herein. As such, rendering should be interpreted broadly unless a narrower meaning is explicitly provided or otherwise clear from the context.

The term "dental object", as used herein, is intended to refer broadly to subject matter specific to dentistry. This may include intraoral structures such as dentition, and more typically human dentition, such as individual teeth, quadrants, full arches, pairs of arches which may be separate or in occlusion of various types, soft tissue (e.g., gingival and mucosal surfaces of the mouth, or perioral structures such as the lips, nose, cheeks, and chin), and the like, as well bones and any other supporting or surrounding structures. As used herein, the term "intraoral structures" refers to both natural structures within a mouth as described above and artificial structures such as any of the dental objects described below. While the design and fabrication of artificial dental structures is the subject of much of the following discussion, it will be understood that any of these artificial structures might be present in the mouth during a scan, either as a result of prior dental work (e.g., a previously restored tooth) or during an evaluation of fit and other aspects of a current procedure. Dental objects may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental objects may also include a "prosthesis" that replaces dentition with removable or permanent structures, such as dentures, partial dentures, implants, retained dentures, and the like. Dental objects may also include "appliances" used to correct, align, or otherwise temporarily or permanently adjust dentition, such as removable orthodontic appliances, surgical stents, bruxism appliances, snore guards, indirect bracket placement appliances, and the like. Dental objects may also include "hardware" affixed to dentition for an extended period, such as implant fixtures, implant abutments, orthodontic brackets, and other orthodontic components. Dental objects may also include "interim components" of dental manufacture such as dental models (full and/or partial), wax-ups, investment molds, and the like, as well as trays, bases, dies, and other components employed in the fabrication of restorations, prostheses, and the like. As suggested above, dental objects may also be categorized as natural dental objects such as the teeth, bone, and other intraoral structures described above or as artificial dental objects such as the restorations, prostheses, appliances, hardware, and interim components of dental manufacture as described above. It will be understood that any of the foregoing, whether natural or artificial, may be an intraoral structure when present within the mouth. Thus, for example, a previous restoration or an implant for a crown might be present within the mouth, and may be an intraoral structure scanned during an intraoral scan.

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified, the term "model", when used alone, may refer to either or both of a physical model and a digital model.

FIG. 1 shows an image capture system. In general, the system 100 may include a scanner 102 that captures images from a surface 106 of a subject 104, such as a dental patient, and forwards the images to a computer 108, which may include a display 110 and one or more user input devices such as a mouse 112 or a keyboard 114. The scanner 102 may also include an input or output device 116 such as a control input (e.g., button, touchpad, thumbwheel, etc.) or a status indicator (e.g., LCD or LED display or light, a buzzer, or the like) to provide status information.

The scanner 102 may include any camera or camera system suitable for capturing images from which a three-dimensional point cloud may be recovered. For example, the scanner 102 may employ a multi-aperture system as disclosed, for example, in U.S. Pat. Pub. No. 20040155975 to Hart et al., the entire contents of which is incorporated herein by reference. While Hart discloses one multi-aperture system, it will be appreciated that any multi-aperture system suitable for reconstructing a three-dimensional point cloud from a number of two-dimensional images may similarly be employed. In one multi-aperture embodiment, the scanner 102 may include a plurality of apertures including a center aperture positioned along a center optical axis of a lens and any associated imaging hardware. The scanner 102 may also, or instead, include a stereoscopic, triscopic or other multi-camera or other configuration in which a number of cameras or optical paths are maintained in fixed relation to one another to obtain two-dimensional images of an object from a number of slightly different perspectives. The scanner 102 may include suitable processing for deriving a three-dimensional point cloud from an image set or a number of image sets, or each two-dimensional image set may be transmitted to an external processor such as contained in the computer 108 described below. In other embodiments, the scanner 102 may employ structured light, laser scanning, direct ranging, or any other technology suitable for acquiring three-dimensional data, or two-dimensional data that can be resolved into three-dimensional data.

In one embodiment, a second scanner such as a PMD [vision] camera from PMD Technologies, may be employed to capture real-time, three-dimensional data on dynamic articulation and occlusion. While this scanner employs different imaging technology (time-of-flight detection from an array of LEDs) than described above, and produces results with resolution generally unsuitable for reconstruction of dental models, such a scanner may be employed to infer motion of, e.g., opposing dental arches with sufficient resolution to select an axis for articulation or otherwise capture dynamic information that can be applied to two or more rigid bodies of a dental object scan. This data may be supplemented with more precise alignment data statically captured from digital or manual bite registration to provide reference or calibration points for continuous, dynamic motion data.

In one embodiment, the scanner 102 is a handheld, freely positionable probe having at least one user input device 116, such as a button, lever, dial, thumb wheel, switch, track ball, mini joystick, touchpad, keypad, or the like, for user control of the image capture system 100 such as starting and stopping scans, or interacting with a user interface on the display 110. In an embodiment, the scanner 102 may be shaped and sized for dental scanning. More particularly, the scanner 102 may be shaped and sized for intraoral scanning and data capture, such as by insertion into a mouth of an imaging subject and passing over an intraoral surface 106 at a suitable distance to acquire surface data from teeth, gums, and so forth. This may include a shape resembling an electric toothbrush or a dental tool, and including an elongated body with an optical port on one end that receives scan data, and user controls on (or near) the other end.

A physical offset may be provided for the optical port that physically maintains an appropriate distance from scanning subject matter. More particularly, the physical offset may prevent the optical port from getting too near the scanned subject matter, which permits a user to maintain proper distance through a steady application of pressure toward the subject matter. The physical offset may be adapted for particular subject matter and may include a simple rod or other rigid form extending toward the optical path of the scanner, or the physical offset may include contoured forms for mating with more complex surfaces. The physical offset may include wheels or plates for slidably engaging a surface of scanned subject matter, or other structures or surface treatments to improve operation in various applications.

The scanner 102 may, through a continuous acquisition process, capture a point cloud of surface data having sufficient spatial resolution and accuracy to prepare dental objects such as restorations, hardware, appliances, and the like therefrom, either directly or through a variety of intermediate processing steps. In other embodiments, surface data may be acquired from a dental model such as a dental restoration, to ensure proper fitting using a previous scan of corresponding dentition, such as a tooth surface prepared for the restoration.

Although not shown in FIG. 1, it will be appreciated that a number of supplemental lighting systems may be usefully employed during image capture. For example, environmental illumination may be enhanced with one or more spotlights illuminating the subject 104 to speed image acquisition and improve depth of field (or spatial resolution depth). The scanner 102 may also, or instead, include a strobe, flash, or other light source to supplement illumination of the subject 104 during image acquisition.

The subject 104 may be any object, collection of objects, portion of an object, or other subject matter. More particularly with respect to the dental fabrication techniques discussed herein, the object 104 may include human dentition captured intraorally from a dental patient's mouth. A scan may capture a three-dimensional representation of some or all of the dentition according to particular purpose of the scan. Thus the scan may capture a digital model of a tooth, a quadrant of teeth, or a full collection of teeth including two opposing arches, as well as soft tissue or any other relevant intraoral and/or extraoral structures. In other embodiments where, for example, a completed fabrication is being virtually test fit to a surface preparation, the scan may include a dental restoration such as an inlay or a crown, or any other artificial dental object. The subject 104 may also, or instead, include a dental model, such as a plaster cast, wax-up, impression, or negative impression of a tooth, teeth, soft tissue, or some combination of these.

Although not depicted, it will be understood that the scanner 102 may have a two-dimensional field of view or image plane where optical data is acquired. It will be appreciated that the term "image plane" as used in this paragraph, refers to a plane in the imaging environment rather than a plane within an optical sensor (such as film or sensors) where an image is captured. The image plane may form any number of two-dimensional shapes according to the construction of the scanner 102, such as a rectangle, a square, a circle, or any other two-dimensional geometry. In general, the scanner 102 will have a depth of field or range of depth resolution for image acquisition within the image plane determined by the physical construction of the scanner 102 and environmental conditions such as ambient light.

The computer 108 may be, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. This system may be operated to capture approximately 1,500 points per image set in real time using the techniques described herein, and store an aggregated point cloud of over one million points. As used herein, the term "real time" means generally with no observable latency between processing and display. In a video-based scanning system, real time more specifically refers to processing within the time between frames of video data, which typically vary according to specific video technologies between about fifteen frames per second and about thirty frames per second. However, it will also be understood that terms such as "video" or "video rate" imply a wide range of possible frame rates associated with such video. While most modern video formats employ a frame rate of 25 to 30 frames per second, early video employed frame rates as low as 8 frames per second, and movies of the early 1900's varied from 12 to 18 frames per second. In addition, it is common for specialized imaging equipment to employ a rate adapted to the computational demands of particular imaging and rendering techniques, and some video systems operate with frame rates anywhere from 4 frames per second (for computationally extensive imaging systems) to 100 frames per second or higher (for high-speed video systems). As used herein, the terms video rate and frame rate should be interpreted broadly. Notwithstanding this broad meaning, it is noted that useful and visually pleasing three-dimensional imaging systems may be constructed as described herein with frame rates of at least ten frames per second, frame rates of at least twenty frames per second, and frame rates between 25 and 30 frames per second.

More generally, processing capabilities of the computer 108 may vary according to the size of the subject 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110.

Communications between the computer 108 and the scanner 102 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the scanner 102 to the computer 108 may be secured. The computer 108 may generate control signals to the scanner 102 which, in addition to image acquisition commands, may include conventional camera controls such as focus or zoom. In addition, the computer 108 may include a network communications interface for connecting to a network such as the dental network described below.

In an example of general operation of a three-dimensional image capture system 100, the scanner 102 may acquire two-dimensional image sets at a video rate while the scanner 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. Such a system employs camera motion estimation to avoid the need for independent tracking of the position of the scanner 102. One useful example of such a technique is described in commonly-owned U.S. application Ser. No. 11/270,135, filed on Nov. 9, 2005, the entire contents of which is incorporated herein by reference. However, it will be appreciated that this example is not limiting, and that the principles described herein may be applied to a wide range of three-dimensional image capture systems.

The display 110 may include any display suitable for video or other rate rendering at a level of detail corresponding to the acquired data. Suitable displays include cathode ray tube displays, liquid crystal displays, light emitting diode displays and the like. In addition, where three-dimensional visualization is desired, the display 110 may include a three-dimensional display using a wide variety of techniques including stereo pair imaging, holographic imaging, and multiplanar or volumetric imaging, each with a number of rendering modalities that may be usefully employed with the systems described herein.

In some embodiments, the display may include a touch screen interface using, for example capacitive, resistive, or surface acoustic wave (also referred to as dispersive signal) touch screen technologies, or any other suitable technology for sensing physical interaction with the display 110.

The touch screen may be usefully employed in a dental office or other context to provide keyboardless processing and manipulation of scanning and any resulting three-dimensional representations. For example, the touch screen may be employed to permit user manipulation of a displayed model, such as panning, zooming, and rotating, through direct physical interaction with the displayed model and any corresponding controls within a user interface. For example, a user may touch a "rotate" button on the display 110, after which placing a finger on the screen and dragging may cause three-dimensional rotation of the displayed model around a corresponding axis (typically perpendicular to the direction of finger motion).

The touch screen may also provide tools for manipulating the digital model. For example, a user may define or specify a cementation void or die spacer. A user may define, edit, or annotate a margin line, such as a computer-generated margin line. A user may define a die and/or ditch a die by recessing one or more regions below the margin line. A user may place arches of a digital dental model into a virtual articulator and articulate the arches. The touch screen may provide one or more tools for virtually designing a dental restoration fitted to a dental model, including fitting to a prepared surface, adjacent teeth, and/or teeth of an opposing arch.

The touch screen may also provide case management controls providing functions such as transmitting a digital model to a dental laboratory, evaluating quality of a digital model or performing other quality control functions as described below, or creating a dental prescription as described, for example, below with reference to FIG. 3.

The image capture system 100 may generally be adapted for real time acquisition and display, e.g., at a video rate, of three-dimensional data, which may be rendered, for example, as a point cloud superimposed on a video image from the scanner 102. For certain types of data acquisition, there may be a significant difference in the processing time required for resolution of a three-dimensional image adequate for two-dimensional perspective rendering (faster) and maximum or optimum resolution that might be achieved with post-processing. In such circumstances, the image capture system 100 may include two different operating modes. In a first operating mode, a relatively low-quality three-dimensional representation may be obtained and rendered in real time, such as within the display 110. In a second operating mode, a relatively high-quality three-dimensional representation may be generated for the source scan data using any desired degree of processing. The second operating mode may recover, through additional post-processing steps, three-dimensional data having greater spatial resolution and/or accuracy. It will be understood that, while two different modes are described, it is not required that the two modes be mutually exclusive. For example, both modes may execute simultaneously on a computer as separate processes or threads, or the data from the first operating mode may be employed to seed the second operating mode with a model for refinement for post-processing. All such variations as would be apparent to one of ordinary skill in the art may be employed with the systems described herein. Either the high-quality representation or the low-quality representation, or both, may be transmitted to a dental laboratory for subsequent steps such as quality control and model fabrication, examples of which are provided below.

In another aspect, the system 100 may provide different levels of accuracy or spatial resolution, each associated with, for example, different degrees of post-processing, computing power, or rate of movement by the scanner 102 over a subject 104. Thus, for example, an entire dental arch may be scanned at a relatively low accuracy, while a surface preparation or other area of diagnostic or treatment significance may be scanned at a relatively higher accuracy which may, for example, require a slower scanning motion or additional post-processing delays. Similarly, certain areas such as the surface preparation may be designated for supplemental post-processing to achieve enhanced accuracy or spatial resolution.

The input or output device 116 may include a feedback device that provides warnings or indicators to an operator of the image capture system 100 with respect to scan quality or progress. The device 116 may include, for example, a buzzer, speaker, light emitting diode, an incandescent light, or any other acoustic, haptic, tactile, or visual signal to notify the operator of an event without requiring the operator to look at the display 110. For example, data quality may be continuously monitored by the system 100, and an alert may be generated when the data quality drops below a quantitative threshold, or data acquisition is lost completely (or different alerts may be provided for each of these events). The evaluation of data quality may depend, for example, on an ability of the system 100 to fit a new data set to existing three-dimensional data, or the ability to resolve two-dimensional image sets into three-dimensional data, or the density of acquired data, or any other objective criterion, either alone or in combination. The evaluation of data quality may also, or instead, be inferred from other parameters such as motion of the scanner 102 or distance from the subject 104. It will be understood that while a data quality indicator may be positioned on the scanner 102 as shown, the device 116 may also, or instead, be positioned at any other location suitable for alerting an operator, which may depend on the type of alert generated (i.e., a visual alert may have different positioning parameters than an audio alert or a tactile alert). In another aspect, the input or output device 116 may provide feedback when data quality is within an acceptable range. In another aspect, the input our output device 116 may provide both positive feedback (good data quality) and negative feedback (poor data quality) so that continuous feedback is available to the operator concerning an ongoing scan.

Figure 2:
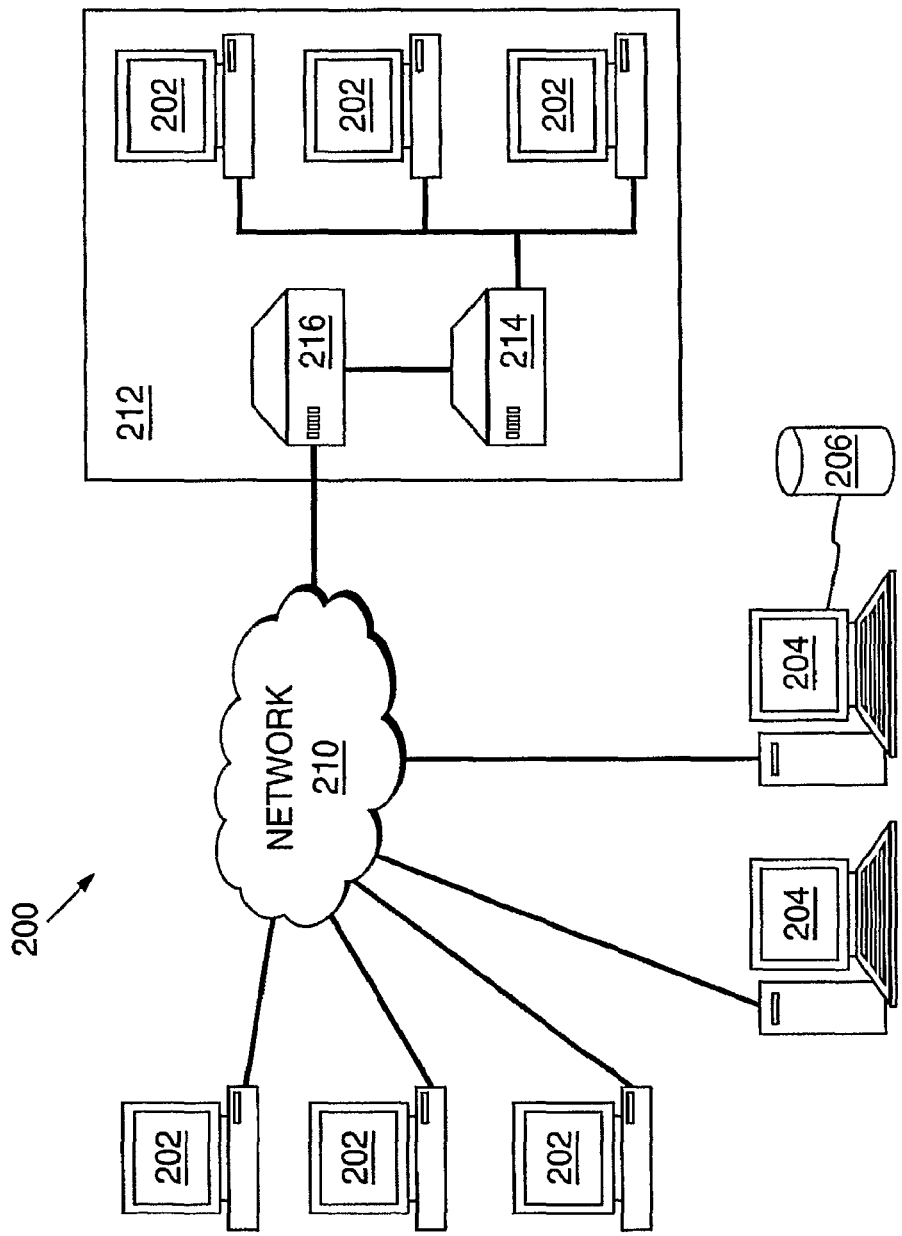
FIG. 2 shows entities participating in a digital dentistry network.

FIG. 2 shows entities participating in a digital dentistry network. As depicted, a network 200 may include a plurality of clients 202 and servers 204 connected via an internetwork 210. Any number of clients 202 and servers 204 may participate in such a system 200. The network 200 may include one or more local area networks ("LANs") 212 interconnecting clients 202 through a hub 214 (in, for example, a peer network such as a wired or wireless Ethernet network) or a local area network server 214 (in, for example, a client-server network). The LAN 212 may be connected to the internetwork 210 through a gateway 216, which provides security to the LAN 212 and ensures operating compatibility between the LAN 212 and the internetwork 210. Any data network may be used as the internetwork 210 and the LAN 212.

The internetwork 210 may include, for example, the Internet, with the World Wide Web providing a system for interconnecting clients 202 and servers 204 in a communicating relationship through the internetwork 210. The internetwork 210 may also, or instead, include a cable network, a satellite network, the Public Switched Telephone Network, a WiFi network, a WiMax network, cellular networks, and any other public, private, and/or dedicated networks, either alone or combination, that might be used to interconnect devices for communications and transfer of data.

An exemplary client 202 may include a processor, a memory (e.g. RAM), a bus which couples the processor and the memory, a mass storage device (e.g. a magnetic hard disk or an optical storage disk) coupled to the processor and the memory through an I/O controller, and a network interface coupled to the processor and the memory, such as modem, digital subscriber line ("DSL") card, cable modem, network interface card, wireless network card, or other interface device capable of wired, fiber optic, or wireless data communications. One example of such a client 202 is a personal computer equipped with an operating system such as Microsoft Windows XP, UNIX, or Linux, along with software support for Internet and other communication protocols. The personal computer may also include a browser program, such as Microsoft Internet Explorer, Netscape Navigator, or Fire-Fox to provide a user interface for access to the internetwork 210. Although the personal computer is a typical client 202, the client 202 may also be a workstation, mobile computer, Web phone, VoIP device, television set-top box, interactive kiosk, personal digital assistant, wireless electronic mail device, or other device capable of communicating over the Internet. As used herein, the term "client" is intended to refer to any of the above-described clients 202 or other client devices, and the term "browser" is intended to refer to any of the above browser programs or other software or firmware providing a user interface for navigating through an internetwork 210 such as the Internet. The client 202 may also include various communications capabilities such as instant messaging, electronic mail, syndication (such as RSS 2.0), Web-based conferencing, Web-based application sharing, Web-based videoconferencing, Voice over IP ("VoIP"), and any other standards-based, proprietary, or other communication technologies, either in hardware, software, or a combination of these, to enable communications with other clients 202 through the internetwork 210.

An exemplary server 204 includes a processor, a memory (e.g. RAM), a bus which couples the processor and the memory, a mass storage device (e.g. a magnetic or optical disk) coupled to the processor and the memory through an I/O controller, and a network interface coupled to the processor and the memory. Servers may be clustered together to handle more client traffic, and may include separate servers for different functions such as a database server, an application server, and a Web presentation server. Such servers may further include one or more mass storage devices 206 such as a disk farm or a redundant array of independent disk ("RAID") system for additional storage and data integrity. Read-only devices, such as compact disk drives and digital versatile disk drives, tape drives, and the like may also be connected to the servers. Suitable servers and mass storage devices are manufactured by, for example, IBM, and Sun Microsystems. Generally, a server 204 may operate as a source of content, a hub for interactions among various clients, and platform for any back-end processing, while a client 202 is a participant in the dental activities supported by the digital dentistry systems described herein. However, it should be appreciated that many of the devices described above may be configured to respond to remote requests, thus operating as a server, and the devices described as servers 204 may participate as a client in various digital dentistry applications.

Focusing now on the internetwork 210, one embodiment is the Internet. The structure of the Internet 210 is well known to those of ordinary skill in the art and includes a network backbone with networks branching from the backbone. These branches, in turn, have networks branching from them, and so on. The backbone and branches are connected by routers, bridges, switches, and other switching elements that operate to direct data through the internetwork 210. For a more detailed description of the structure and operation of the Internet 210, one may refer to "The Internet Complete Reference," by Harley Hahn and Rick Stout, published by McGraw-Hill, 1994. However, one may practice the present invention on a wide variety of communication networks. For example, the internetwork 210 can include interactive television networks, telephone networks, wireless voice or data transmission systems, two-way cable systems, customized computer networks, Asynchronous Transfer Mode networks, and so on. Clients 202 may access the internetwork 210 through an Internet Service Provider ("ISP", not shown) or through a dedicated DSL service, ISDN leased lines, T1 lines, OC3 lines, digital satellite service, cable modem service, or any other connection, or through an ISP providing same. Further, the internetwork 210 may include a variety of network types including wide-area networks, local area networks, campus area networks, metropolitan area networks, and corporate area networks.

In an exemplary embodiment, a browser, executing on one of the clients 202, retrieves a Web document at an address from one of the servers 204 via the internetwork 210, and displays the Web document on a viewing device, e.g., a screen. A user can retrieve and view the Web document by entering, or selecting a link to, a URL in the browser. The browser then sends an http request to the server 204 that has the Web document associated with the URL. The server 204 responds to the http request by sending the requested Web document to the client 202. The Web document is an HTTP object that includes plain text (ASCII) conforming to the HyperText Markup Language ("HTML"). Other markup languages are known and may be used on appropriately enabled browsers and servers, including the Dynamic HyperText Markup Language ("DHTML"), the Extensible Markup Language ("XML"), the Extensible Hypertext Markup Language ("XHTML"), and the Standard Generalized Markup Language ("SGML").

Each Web document usually contains hyperlinks to other Web documents. The browser displays the Web document on the screen for the user and the hyperlinks to other Web documents are emphasized in some fashion such that the user can identify and select each hyperlink. To enhance functionality, a server 204 may execute programs associated with Web documents using programming or scripting languages, such as Perl, C, C++, C#, or Java, or a Common Gateway Interface ("CGI") script to access applications on the server. A server 204 may also use server-side scripting languages such as ColdFusion from MacroMedia or PHP. These programs and languages may perform "back-end" functions such as order processing, database management, and content searching. A Web document may also contain, or include references to, small client-side applications, or applets, that are transferred from the server 204 to the client 202 along with a Web document and executed locally by the client 202. Java is one popular example of a programming language used for applets. The text within a Web document may further include (non-displayed) scripts that are executable by an appropriately enabled browser, using a scripting language such as JavaScript or Visual Basic Script. Browsers may further be enhanced with a variety of helper applications to interpret various media including still image formats such as JPEG and GIF, document formats such as PS and PDF, motion picture formats such as AVI and MPEG, animated media such as Flash media, and sound formats such as MP3 and MIDI. These media formats, along with a growing variety of proprietary media formats, may be used to enrich a user's interactive and audio-visual experience as each Web document is presented through the browser. In addition, user interaction may be supplemented with technologies such as RSS (for syndication), OPML (for outlining), AJAX (for dynamic control of a web page), and so forth. The term "page" as used herein is intended to refer to the Web document described above, as well as any of the above-described functional or multimedia content associated with the Web document. A page may be employed to provide a user interface to the digital dentistry systems described herein. In addition, one or more applications running on a client 202 may provide a user interface for local and/or networked digital dentistry functions as described herein.

In FIG. 2, each client 202 represents a computing device coupled to the internetwork 210. It will be understood that a client 202 may be present at a location associated with digital dentistry such as a dental laboratory, a rapid manufacturing facility, a dental office, and/or a dental data center. Each of these potential participants in a digital dentistry system will now be described in greater detail.

One of the clients 202 may reside at a dental office. The dental office may include any office or other physical facility that provides dental care including individual dentist offices, dental group offices, retail dental centers, university dental schools, and the like. A dental patient may visit the dental office for a routine check up or cleaning, or for a visit scheduled due to oral discomfort, dental injury, or the like.

During the dental visit, a dentist may examine the dental patient and provide a dental assessment, such as the need for a restoration, tooth extraction, or the like. The dental office may include a three-dimensional scanner, such as any of the scanners described above, which the dentist may use to capture a three-dimensional digital representation of the dental patient's dentition including scans both before and after one or more tooth surfaces have been prepared for a dental object such as a restoration or the like. While a scan may be performed in the context of a specific dental issue, such as a planned restoration, the dentist may also capture scans during routine visits so that a dental history for the dental patient is accumulated over time. Using the client 202, which may include the image capture system 100 described above, the dentist may obtain one or more three-dimensional representations and, after discussing treatment with the dental patient, input any relevant dental prescription information. The dentist may then electronically transmit the three-dimensional representations, along with the prescription, to a dental laboratory or other fabrication facility using a network such as the internetwork 210 described above. In general, an electronic dental prescription, as used herein, includes a dental prescription in electronic form along with any three-dimensional data such as tooth surfaces before and after surface preparation, teeth in occlusion, and so forth. Additional data, such as x-ray, digital radiographic, or photograph data may be incorporated into the electronic dental prescription, or otherwise used with the systems and methods described herein. In certain instances, an electronic dental prescription may instead refer exclusively to the prescription data. In general, the meaning should be clear from the context, however, in the absence of explicit guidance, the broadest possible meaning is intended.

As a significant advantage, a practicing dentist may maintain a history of three-dimensional representations of dentition and surrounding soft tissue for each dental patient.

Where a new procedure, such as a restoration, is scheduled for the patient, the dentist may pre-fabricate a temporary restoration using historic dental data. The temporary restoration may be fabricated for example, at the dental office where the procedure is scheduled using a three-dimensional printer and/or a copy milling machine, or at a remote facility such as the dental laboratory or rapid manufacturing facility described below. In one aspect, a scan may be obtained of a prepared surface during the scheduled visit, and the temporary restoration (or a final restoration) may be fabricated, such as at the dental office during the visit, by combining historical three-dimensional data with a three-dimensional representation of the prepared surface. In another embodiment, a treating dentist may shape the surface preparation to receive a pre-fabricated temporary restoration.

More generally, the client 202 at the dental office may be coupled in a communicating relationship with a client 202 at one or more of a dental laboratory, another dental office, a rapid manufacturing facility, and/or a dental data center for communication of three-dimensional representations of dental subject matter and related information. This dental network may be usefully employed in diagnosis, case planning, consultation, evaluation, and the like. Participation may include, for example, consultation, online or distance collaboration, approval, payment authorization, or any other collaborative or unilateral participation, examples of which are provided throughout this description. Thus there is disclosed herein methods and systems for sharing digital dental data, such as digital dental impressions captured using the techniques described above. This may permit a wide array of collaborative communications using a shared view of dentition or related digital models. For example, a dentist may collaborate with another dentist, a dental technician at a dental laboratory, an oral surgeon, a technician at a rapid manufacturing facility, or any other participant in a dental network at a remote location using a shared view of a patient's dentition. Various dental specialists may participate from remote (or local) locations, such as a periodontist, a prosthodontist, a pedodontist, an orthodontic specialist, an oral and maxillofacial surgery specialist, an oral and maxillofacial radiology specialist, an endodontist, and/or an oral and maxillofacial pathologist. Tools may be provided, such as collaborative tools, for sharing control of model manipulation, sectioning, rearranging, marking, and visualizing or simulating proposed clinical procedures. Each participant may view a rendering of the three-dimensional representation of dentition from a common or shared point of view. Control of the view and any modeling tools may be passed among participants, as well as a cursor or command prompt shared by participants within a user interface. In one aspect, this system forms a collaborative dental environment in which a three-dimensional representation of a dental patient's dentition is shared among participants. Communications among participants may include any network-supported communications protocol including electronic mail, instant messaging, Internet Relay Chat, Voice-over-IP, and the like, as well as conventional teleconferencing.

Turning next to the dental laboratory, a dental laboratory may provide a fabrication resource for dental practitioners. A conventional dental laboratory may have a number of production departments specializing in various dental objects such as complete dentures, partial dentures, crowns and bridges, ceramics, and orthodontic appliances. A dental laboratory may employ trained technicians to perform various tasks associated with filling a dental prescription such as preparing dental models, dies, articulated models, and the like from impressions and occlusal registrations received from dentists.

Typically, a dentist submits an order with specific instructions (a prescription) to a dental laboratory, and the laboratory fabricates the corresponding dental object(s) for use by the dentist. A client 202 at a dental laboratory may be coupled in a communicating relationship with a client 202 at one or more of a dental office, another dental laboratory, a rapid manufacturing facility, and/or a dental data center for communication of three-dimensional representations of dental subject matter and related information. This dental network may be usefully employed in diagnosis, case planning, consultation, evaluation, and the like.

Dental laboratories may for example create restorative products such as crowns and bridges. A traditional crown formed of gold, other metal alloys, or ceramic may replace all visible areas of a tooth. An onlay is a partial crown that does not fully cover the visible tooth. Crowns may include a precision attachment incorporated into the design that may receive and connect a removable partial denture. Inlays are restorations fabricated to fit a prepared tooth cavity and then cemented into place. A bridge is a restoration of one or more missing teeth, such as a fixed partial, a three unit bridge, or the like. A bridge may be permanently attached to the natural teeth or attached to custom-made or prefabricated posts and cores that are first cemented into the roots.

Another major area of dental objects includes reconstructive products, most typically dentures. Partial dentures are a removable dental prosthesis that replaces missing teeth and associated structures. Full dentures substitute for the total loss of teeth and associated structures. Some dental labs also make precision attachments that connect a crown to an artificial prosthesis. Implants are fixtures anchored securely in the bone of the mouth to which an abutment, crown or other dental object can be attached using screws, clips, or the like. This may include, for example, a titanium root replacement integrated with the bone, an abutment or transfer coping, and an implant secured to the abutment. Implant procedures also typically involve a healing abutment to assist with healing of affected soft tissue and to maintain positioning of teeth while the root replacement attaches to the bone (which may take several months). An additional impression may be taken of the implant using an impression coping or abutment after it has attached to the bone for preparation of a final restoration.

A dental laboratory may also manufacture cosmetic products such as ceramic or composite resin veneers and crowns. Veneers are thin coverings cemented to the front of the tooth for aesthetic affect. Crowns are designed to cover the entire tooth preparation and will resemble natural teeth. Composite or ceramic inlays and onlays may be manufactured to replace amalgams and give teeth a more natural appearance. Orthodontic appliances move existing teeth to enhance function and/or appearance.

In general, the procedures described above involve transfer of a dental impression to a laboratory for fabrication of the final dental object. In some cases, such as implants, a number of impressions may be taken over the course of treatment. Using a scanner such as that described above, a dentist may capture an accurate three-dimensional representation of dentition and surrounding tissue and transmit this digital version of the dental impression to a dental laboratory using a network such as the internetwork 210 described above. The dental laboratory may receive the data and proceed with any appropriate fabrication. In various procedures, the three-dimensional representation may include data from two or more scans, such as an initial three-dimensional representation of dentition prior to any dental work, and a prepared three-dimensional representation of the dentition after one or more tooth surfaces have been prepared for the dental object(s).

The surface preparation may provide guidance to the laboratory concerning fit of the restoration or other dental object to the tooth surface, and the initial scan may provide valuable information concerning the appropriate dimensions for the final dental object and its relationship to surrounding teeth. A dentist may also optionally specify a number of parameters for the dental laboratory as described in various examples below.

Where a particular dental object is temporary, or will be covered by another dental object at a subsequent dental visit, the object may be fabricated with one or more characteristics that improve scanning of any exposed surfaces once the object is placed within a dental patient's mouth. For example, an object such as an impression coping, fixture, or healing abutment may be fabricated with scanning-optimized surfaces such as an optical or textured finish. An optical finish may, for example, include randomly (or pseudo-randomly) distributed coloration such as black or other high-contrast dots. A textured finish may, for example, include a pseudo-random texture or one or more discrete landmarks.

It will be appreciated that in certain embodiments the dental laboratory may be an in-office dental laboratory physically located within or near a dental office where a dental patient is receiving treatment. In various embodiments, the in-office dental laboratory may provide facilities for a subset of dental objects described above, such as those most commonly used by a particular dentist.

Rapid manufacturing facilities may also be employed with the systems described herein. A rapid manufacturing facility may include equipment for designing and/or fabricating dental objects for use in dental procedures. A client 202 at a rapid manufacturing facility may be coupled in a communicating relationship with a client 202 at one or more of a dental office, another dental laboratory, a rapid manufacturing facility, and/or a dental data center for communication of three-dimensional representations of dental subject matter and related information. This dental network may be usefully employed in diagnosis, case planning, consultation, evaluation, and the like.

Rapid manufacturing facilities may include, for example one or more stereo lithography apparatuses, three-dimensional printers, computerized milling machines, or other three-dimensional rapid prototyping facilities or similar resources. A particular facility may include one or more of a number of different types of machines which may be scheduled for various fabrication jobs received through the internetwork 210. In one embodiment, a single facility may provide a large number of machines along with suitably trained technical personal to provide a centralized fabrication facility. In another embodiment, machines may be distributed at various locations, including one or more machines within dental offices and dental laboratories. Where copings, crowns, or the like are to be finished at the rapid manufacturing facility rather than, for example, a dental laboratory, the rapid manufacturing facility may also include machinery such as pressing machines and electroplating machines.

More generally, a dental fabrication facility may include one or more of the rapid manufacturing facilities, dental laboratory facilities, or in-office dental laboratories described above, either alone or in combination.

A dental data center may provide a hub for a digital dentistry network. A server 204 at a dental laboratory may be coupled in a communicating relationship with a client 202 at one or more of a dental office, a dental laboratory, a rapid manufacturing facility, and/or another dental data center for communication of three-dimensional representations of dental subject matter and related information. This dental network may be usefully employed in diagnosis, case planning, consultation, evaluation, and the like. The dental data center may, for example operate as an intermediary between dentists, laboratories, and fabrication facilities to provide a common repository for new dental jobs from a dental office, which may be distributed to available resources at one or more dental laboratories and/or rapid fabrication facilities. In addition to scheduling and workload allocation, the dental data center may provide various value-added services such as quality control for incoming three-dimensional representation, financial transaction management, insurance authorization and payment, and the like.

The dental data center may coordinate a number of transactions within a digital dentistry network. For example, the dental data center may engage in continuous bidding for fabrication work in order to ensure competitive pricing for fabrication facility and dental laboratory work sourced from the dental data center. As another example, the dental data center may provide status updates concerning a fabrication job to a dentist or other participant, including up-to-date information such as job received, job at fabrication facility, job at dental laboratory, model completed, waxing completed, investing completed, casting completed, porcelain build-up completed, restoration completed, finishing, shipping, and so forth. The dental data center may provide a web-based work-in-progress interface through which a dentist may monitor progress. Other known systems, such as electronic mail alerts or RSS updates, may be used to provide status updates to dentists or other interested parties. While a dental data center may be usefully employed with the digital dentistry systems described herein, it will also be understood that various dental networks may operate independently between parties, such as between a dental office and a dental laboratory or between a dental laboratory and a rapid manufacturing facility, or between a number of dental offices and a rapid manufacturing facility, without a centralized server at a dental data center. All such embodiments are intended to fall within the scope of this disclosure. Further, it will be understood that a wide array of software platforms, communications protocols, security protocols, user interfaces, and the like are known, and may be suitably adapted to a web-based, web-services based, or other dental data center as described herein.

A digital dentistry network may include other participants, such as a consulting dentist, and oral surgeon, an insurer, a federal or state regulator or oversight entity, or any other dental entity. Each of these participants may communicate with other participants in the digital dentistry network through use of a client 202. Through this digital dentistry network, various methods and systems may be deployed. For example, in one aspect a three-dimensional representation and a dental prescription may be electronically transmitted to an insurer through the network, and the insurer may respond with authorization to perform the specified dental procedure (or a denial, which may include any reasons for the denial), including fabrication of any related dental objects. The insurer may maintain an electronic copy of three-dimensional representations relevant to the authorization, such as an image of the tooth surface prepared for the procedure. The insurer may also render payment, or authorize payment, to a treating dentist. The insurer may also, or instead, render payment to related entities, such as a dental laboratory or rapid manufacturing facility, for fabrication services provided. In one common practice, the insurer makes a single payment to the treating dentist who may in turn contract desired vendors for fabrication services. However, the insurer may render payments separately to one or more parties involved including a dentist, a dental patient, a dental laboratory, a rapid manufacturing facility, and so on.

In one aspect, dental laboratory procedures may be improved by fabricating a kit of components for use by a dental laboratory in subsequent fabrication of a final restoration, prosthesis, or the like. For example, a kit may include one or more of a die, a quad model, an opposing quad model, a full arch model, an opposing arch model, a base, a pre-articulated base, a waxup, and so forth. More generally, the kit may include one or more pre-cut components, pre-indexed components, and pre-articulated components for assembly into a dental model, such as a model adapted for use with an articulator. The kit may also, or instead, include various interim components of dental manufacture, such as required or commonly used components for particular procedures, e.g., the PFM crown kit, the bridge kit, and so on. All or some of these components may be automatically fabricated as a kit by a production facility specializing in high-throughput such as the rapid manufacturing facility described above, and the kit may be forwarded to a dental laboratory specializing in creation of final restorations and the like. This approach leverages the relative expertise of these two participants in a digital dentistry network, and may achieve significant decreases in cost and time to a final restoration or other dental object. Alternatively, a dentist may determine and directly fabricated any required kit components using, for example, an in-house three-dimensional printer. In one aspect, a group of different kits may be established for different dental work, so that a dental prescription automatically triggers fabrication of the corresponding kit.

Figure 3:
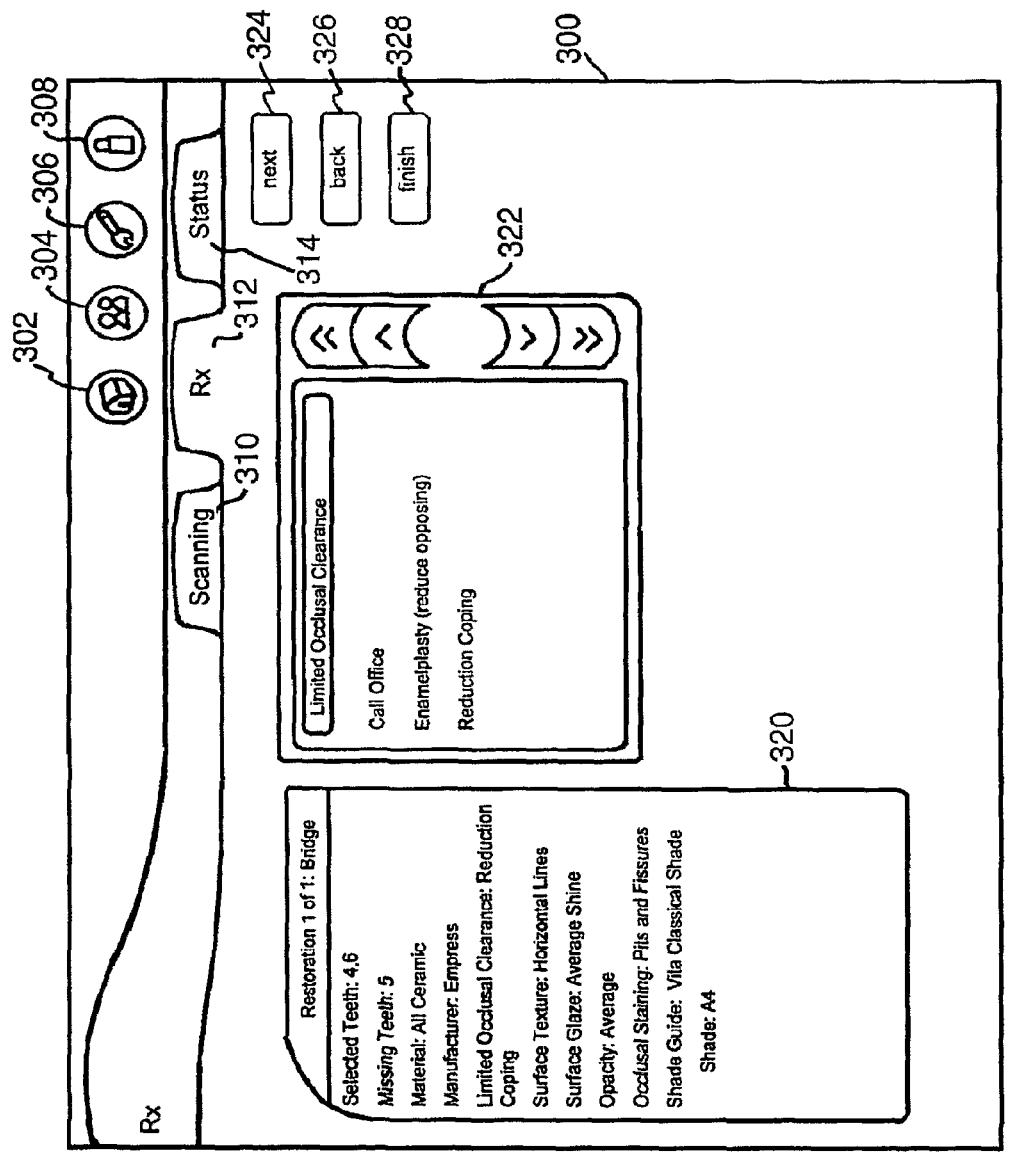
FIG. 3 shows a user interface that may be used in a digital dental system.

FIG. 3 shows a user interface that may be used in a digital dental system. The user interface may be presented, for example, as a Web page viewed using a Web browser, or as an application executing on one of the clients 202 described above, or as a remotely hosted application, or as a combination of these.

The interface 300 may include navigation features such as a home control 302, a name directory control 304, a toolbox control 306, and a security control 308. Each of these features may direct the interface 300 to a different functional area. For example, the home control 302 may access a top level menu that provides access to, for example, system login, data source selection, hardware/software configuration, administrative tools, and so forth. The name directory control 304 may access a directory of patients, physicians, dental laboratories, rapid manufacturing facilities and like, and permit searching, data input, and so forth. The directory may, for example, provide access to patient dental records and history, contact information, and the like. The toolbox control 306 may provide access to tools for scanning, case planning and management, scheduling, and the like. The security control 308 may provide access to account management, communications configuration, and other security-oriented features and functions of a digital dentistry system.

Within each main area of top-level navigation, the interface 300 may provide a number of tabs, such as the scanning tab 310, the prescription tab 312, and the status tab 314 depicted in FIG. 3. The scanning tab 310 may, for example, invoke an interface for controlling operation of an image capture system 100 such as that described above in reference to FIG. 1. The prescription tab 312 may, for example, invoke an interface that permits specification of a restoration or other dental object, including a specification of teeth being treated, treatment type, manufacturer, and details of the dental object including color, material, texture, and so forth. The interface of the prescription tab 312 may also include tools for transmitting a prescription, along with any three-dimensional data obtained from scans of a patient, to a dental laboratory, dental data center, rapid manufacturing facility, or the like The status tab 314 may, for example, invoke an interface for obtaining or updating status information on a case such as the fabrication status of a prescription (e.g., prescription and scan received, scan evaluated and approved, models complete, object fabricated, object shipped to dentist, and so forth).

FIG. 3 depicts in more detail a prescription window of the interface 300, as accessed by selecting the prescription tab 312. This window may show current data for a prescription within a text window 320. A scroll bar 322 or other control may be provided for selecting options relating to a prescription. In operation, and by way of example only, a feature of the prescription, such as the material or manufacturer, may be highlighted within the text window 320, and options for that feature may selected from the scroll bar 322. The window may also include additional navigational or process controls such as a next button 324, a back button 326, and a finish button 328, which may be used to navigate through one or more different windows of a prescription and/or case planning interface. This may include, for example, input of patient data, selection of a dental laboratory, scheduling of dental visits, and the like. It will be understood that the above interface 300 is an example only and that other hierarchical arrangements of functions, and/or arrangements of data and controls within a particular interface, are possible and may be employed with a digital dental system as described herein. For example, the interface may control scanning, marking or annotation of scanned models, case planning, access to databases of patient records and dental data, preparation of prescriptions, analysis of dentition, scheduling, management of patient data, communications with remote fabrication facilities, and so forth. Any user interface or combination of user interfaces and user interface technologies suitable for a digital dental system as described herein may be employed without departing from the scope of this disclosure. As such, a user interface 300 should be understood more generally with reference to the systems and methods described herein, and not by specific reference to the example interface shown in FIG. 3.

Having described a number of aspects of a digital dentistry system and network, along with various participants in such a network, specific uses of the system will now be discussed in greater detail.

Figure 4:
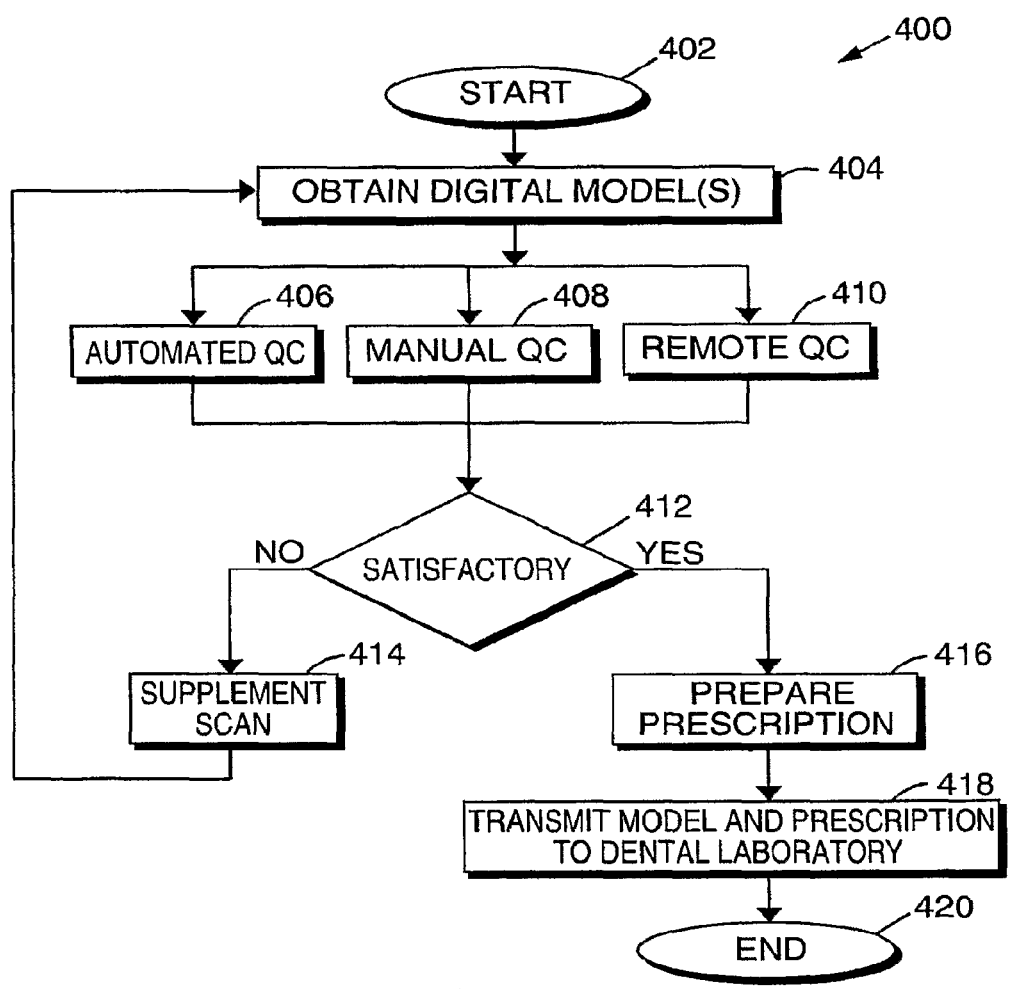
FIG. 4 depicts a quality control procedure for use in a digital dental system.

FIG. 4 depicts a quality control procedure for use in a digital dental system. The process 400 may start 402 by obtaining a digital model, such as a three-dimensional representation of dental subject matter as described generally above.

The digital model may include a single model, such as a digital model of dentition prior to any dental work, such as for archival or comparison purposes. This may also, or instead, be a digital model of dentition including one or more prepared surfaces, such as a single tooth surface prepared for a crown, or a number of tooth surfaces prepared for a multi-unit bridge. This may also include a scan of bite registration. For example, a scan may be obtained of the teeth of a dental patient in centric relation, centric occlusion, or with maximum intercuspation, in protrusion (e.g., for sleep apnea guards), in lateral excursions, or in any other static orientation useful for any of the dental procedures described herein. As a significant advantage, the upper and lower arches may be treated as rigid bodies, thus permitting relative three-dimensional orientation for a full bite registration to be obtained from a scan of a relatively small region of the upper and lower arches while in occlusion, such as centric occlusion. Thus for example, a three-dimensional scan that spans the two arches, such as a scan of the exterior surfaces of one or two teeth in a buccal or labial area, may be used to register bite. In addition, the digital model may include motion information describing the relative motion of, e.g., an upper and lower jaw throughout one or more jaw motions such as opening and closing the mouth or simulated chewing. Such motion data may, for example, be obtained through a variety of techniques suitable for tracking three-dimensional motion, which may include extrapolation from video data, use of transmitters on the moving jaws, mechanical or electromechanical sensors and/or transmitters, and so forth. Motion data may also be inferred by capturing orientation data for the jaws in a variety of positions. Motion data may be employed, for example, to derive the position of TMJ condyle paths of rotation and translation, or to provide input to a virtual or conventional dental articulator.

In addition, dynamic three-dimensional data may be obtained and used. As noted elsewhere herein, some systems permit direct three-dimensional video capture. However, other techniques may be employed to capture dynamic data. For example, in one example process, two opposing arches may be brought into natural occlusion. The dental patient may then slide the arches forward and back and from side to side, during which the scanner may capture relative motion of the two rigid bodies defined by the two opposing arches. The captured data may be used to characterize and animate a three-dimensional transformation that captures the full excursion of the dentition. This data may, in turn, be registered to detailed scans of the opposing arches. As a further use of this type of data, the excursion data may be used in combination with detailed arch data to provide a cutting tool or path for occlusal surfaces of a restoration. Thus, occlusal surfaces may be measured or otherwise determined during a scan, and applied to define surfaces of a restoration. Using various CAD modeling tools, the restoration may be further refined, such as by shaping side walls of the restoration, adding visually appealing and/or functional cusps to the occlusal surfaces, and so forth. Thus in one aspect there is disclosed herein a method for determining one or more occlusal surfaces of a dental restoration using dynamic three-dimensional data acquired during a scan. The method may include obtaining a three dimensional model of two opposing arches of a patient's dentition, obtaining excursion data for the two opposing arches, preparing a tooth surface of the dentition for a restoration, and determining an occlusal surface of the restoration using the excursion data and the three-dimensional model.

More generally, any digital model or other data useful in dental procedures, restorations, and the like as described herein may be obtained in step 404.

Once a digital model (or models) is obtained in step 404, the process 400 may proceed to one or more quality control steps as depicted in steps 406-410.

This may include automated quality control, as shown in step 406, which may be simple quantitative analysis such as measures of accuracy, variability, or density of three-dimensional surface data for a digital model. This may also, or instead, include more sophisticated, automated analyses such as adequacy and/or suitability of margins and prepared surfaces for an anticipated restoration. For example, an automated quality control tool may examine a prepared tooth surface to ensure that a margin line is present all the way around a preparation, or examine the prepared surface to ensure that adequate material has been removed to accommodate a restoration. Similarly, an automated process may locate areas of potential problems, such as occlusal high spots, occlusal clearance, occlusal irregularities, areas of poor margin preparation, areas of inadequate tooth removal, improper taper, improper draw path or removal path for a multiple unit preparation, inappropriate contour, and so forth.

In one aspect, quality control may include real time feedback during a scan, or between successive scans. The feedback may be rendered with suitable visualizations on a display to permit immediate observation and correction by a dentist. Thus it will be appreciate that, while depicted in FIG. 4 as a post-scanning operation, quality control may be implemented at any time in a digital dentistry process, or throughout the entire process. Real time feedback may include for example, textual annotations identifying teeth as they are recognized within a scan, and providing one or more dimensions of a tooth, or an analysis of contour, clearance relative to adjacent teeth, or a position of the tooth relative to other teeth or relative to a global coordinate system. By providing this information in real time within the context of a single dental visit, treatment may be generally improved by reducing or eliminating a need for follow up scans.

In another aspect, quality control may include an evaluation of suitability of a surface preparation, or a restoration or other dental object prepare for the restoration, for manufacturing using one or more techniques, including three-dimensional printing, milling, stereo lithography, and or conventional dental fabrication, or various combinations of these.

Although not depicted in FIG. 4, it will be appreciated that quality control may be semi-automated. Thus, for example, a user interface may provide a number interactive, three-dimensional tools such as markup tools that a dentist or other dental professional may use to measure, mark, annotate, or otherwise manipulate a digital model to evaluate suitability for subsequent processing and the creation of a physical dental object such as a restoration.

As shown in step 408, quality control may include manual quality control. For example, a dentist may inspect a scan in an interactive, three-dimensional environment to visually identify, e.g., holes or areas of incomplete scan needed for an intended dental procedure. The dentist may employ various features, such as rotation, zooming, and panning to inspect various surfaces of the three-dimensional digital representation from a scan.

As shown in step 410, quality control may include remote quality control. For example, after completing a scan, a dental office may transmit a digital model to a dental laboratory or a fabrication facility for evaluation of adequacy of the scan. As a significant advantage, the recipient, such as a dental laboratory may provide immediate feedback to a dentist while a dental patient is still in the dental office, or still in a dentist's chair at a dental office, thus avoiding a need to schedule repeat visits for additional surface scanning or surface preparation. A dental laboratory may inspect a prepared surface to ensure that a restoration can be fit to the prepared surface, or that there is adequate space (especially thickness) for a restoration or other dental object. The dental laboratory may also evaluate color and suggest shade matching for a dentist. The dental laboratory may request manual marking of a margin by a dentist where the margin is not visible on a prepared tooth surface. The dental laboratory may also apply separate standards for data quality (density, accuracy, surface continuity, feature detail, etc.), and may request additional or new scan data consistent with its own specifications. The dental office may transmit a case plan prior to (or during) transmission of a scan, which may permit more detailed analysis of the scan data by the recipient. Thus, for example, a dental laboratory may evaluate suitability of the scan and/or surface preparation for a type of restoration and any prescribed components (e.g., full ceramic, porcelain-fused-to-metal, etc.). Where the dental laboratory can quickly generate an accurate or rough model for a restoration or other dental object according to any fabrication or end use constraints, the rough model may, in digital form, be virtually fit to the prepared surface, and feedback may be provided to a dentist such as an identification of regions requiring further reduction.

Quality control, whether automated or manual, and whether local or remote, may include a variety of different dental evaluations. For example, a prepared tooth in an arch that will receive a restoration may be evaluated to determine whether there is adequate space for cement to bond the restoration to the prepared tooth surface. As another example, a dentist may visually confirm accuracy of a scan by inspection for gross errors or omissions such as holes, gaps, distortions, twists, and the like. The dentist may also visually inspect margin lines on surface preparations, and may annotate margins for identification by a dental laboratory or other fabrication facility. Similarly, a dental laboratory may, during a quality control evaluation, request that the dentist identify the margins on a surface preparation where the margin lines are not self-evident.

Feedback from a quality control step, whether automated or manual, and whether remote or local, may include various forms of feedback. For example, an evaluation may conclude with an identification of regions of a prepared tooth surface requiring additional preparation or reduction, or regions of a digital model requiring additional or supplemental scanning due to incomplete, erroneous, or potentially erroneous data, which may be identified, for example, by comparison to models of expected shape for dentition, surface preparations, and the like. An evaluation from a dental laboratory may request new data, or additional shaping of a prepared surface. An evaluation from a dental laboratory may include a request for an oral consultation. In addition other dental professionals such as a consulting dentist, an oral surgeon, a dental specialist, or a laboratory technician may be called upon for evaluation, approval, and/or recommendations. Feedback may be presented to a dentist in a number of forms. For example, the feedback may include text or audible narrative concerning additional scanning, additional surface preparation, or requests for confirmation. The feedback may be graphical feedback provided by highlighting questionable or erroneous areas of a preparation within a rendered display of scan data. The feedback may identify corrective action on a scan or a surface preparation. The feedback may identify a margin line which may be displayed on a two-dimensional rendering of a three-dimensional representation, and a user interface may permit the margin line to be edited or confirmed. The feedback may include a visual display with regions of inadequate margin highlighted, such as through use of color, texture, or explicit annotations, arrows, callouts, or the like, and any combination of these.

It will be understood that the quality control steps indicated in FIG. 4 are not mutually exclusive. That is each of the quality control steps 406-410 may be performed during the process 400, such as in sequence or in parallel (as where a dentist and a laboratory evaluate a scan simultaneously), and all such variations are intended to fall within the scope of this disclosure.

Any of the quality control steps above may advantageously be performed while a dental patient is still present at a dental office, or while the patient is still in a dental chair, thus reducing or eliminating the need for follow up dental visits for additional scanning.

After one or more quality control steps 406-410, a determination may be made as to whether a scan and/or surface preparations are satisfactory. If the data is not satisfactory, the process 400 may proceed to step 414 where the digital model may be supplemented or replaced with new scan data. This may include, for example, new scanning to replace apparently erroneous or inadequate scan data, or a new scan of the dental subject matter following, e.g., additional surface preparation consistent with errors identified during quality control. The process 400 may then return to step 404 where a new digital model is obtained.

If it is determined in step 412 that the data is satisfactory, the process 400 may proceed to step 416 where a dentist may prepare a prescription. The prescription may include, for example, a dental patient identification, an identification of one or more teeth being treated, a type of treatment (e.g., for a restoration, one or more of a bridge, a crown, an inlay, a laminate veneer, an onlay, or a temporary), an identification of missing teeth (if appropriate), a material or fabrication technology (e.g., full ceramic, cast metal, PFM, etc.), an alloy type (e.g., for a PFM crown), a manufacturer (e.g., Cercon, Cerec, Empress, Everest, Lava, Procera, etc.), limited occlusal clearance (e.g., enamalplasty, reduction coping, etc.), a shade guide (e.g., Vita 3D Master, Vita Classical, etc.), a surface texture, a surface glaze, an opacity, an occlusal staining, dental notes, and any other information relevant to identification or preparation of the dental object. For example, for a crown the specification may include a material type, a design (such as metal band, 360-degree facial butt porcelain shoulder, facial butt porcelain shoulder, metal occlusal surface, or no metal showing), a return (e.g., biscuit bake, finish, metal try-in, etc.). Each specification may include subspecifications. For example, a metal band crown may be specified as having the metal band located at a buccal location, a lingual location, or 360-degree.

As shown in step 418, once the prescription has been completed, the digital model and prescription may be uploaded to a dental laboratory or other fabrication facility using, for example, the dental network described above. The process 400 may then end, as shown in step 420.

It will be understood that numerous variations and modifications to the above process 400 may be used. For example, the prescription may be prepared at a different point in the process, such as before scanning so that the prescription data may be used to evaluate sufficiency of the scan data. As another example, each digital model (e.g., native tooth surfaces, bit registration, prepared tooth surfaces) may be separately presented to one or more quality control steps, or the entire digital model may be obtained prior to any quality control analysis. All such variations and modifications are intended to fall within the scope of the methods and systems described herein.

Figure 5:
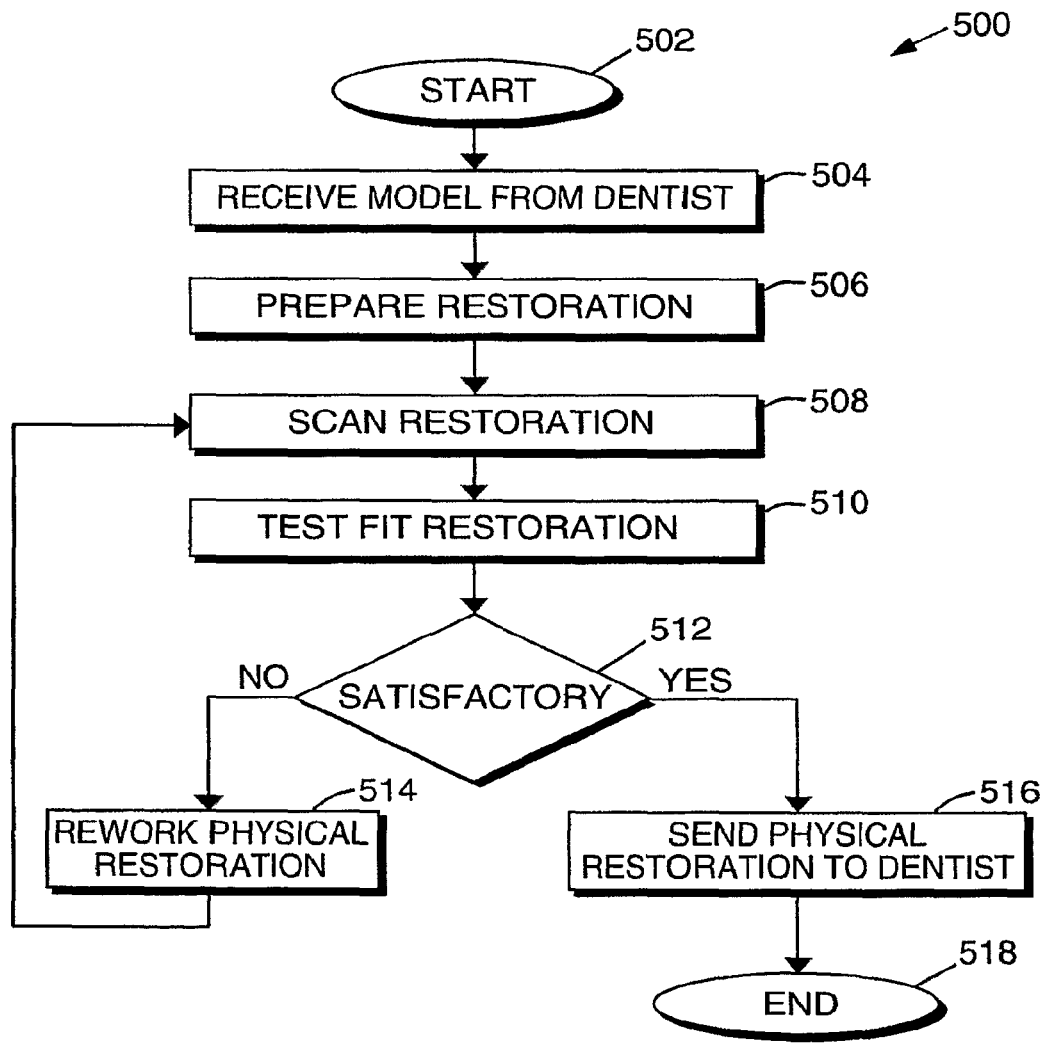
FIG. 5 shows a dental laboratory procedure using a digital dental model.

FIG. 5 shows a dental laboratory procedure using a digital dental model. While described as a dental laboratory procedure, it will be understood that the fabrication and quality control procedures described with reference to FIG. 5 may be performed by any fabrication facility including a dental fabrication facility such as a dental laboratory equipped to receive digital dental data, a model production laboratory (such as a rapid fabrication facility, milling facility, and the like), an in-office dental laboratory at a dental office, or any other dental fabrication facility. The fabrication facility may include a remote facility accessible through the dental network, and digital dental data may be communicated to the fabrication facility directly or through a hub for dental data such as the dental data center described above.

As shown in step 504, the process 500 may start 502 by receiving a digital model from a dentist or other source. This may include, for example, a digital model, such as a digital surface representation obtained using the image capture system 100 described above, of a surface prepared for a restoration such as a crown, or any other dental object.

As shown in step 506, the dental laboratory may design and/or fabricate a restoration or other dental object based upon the digital model received in step 504. This may include a variety of fabrication techniques, including working from a physical cast of a dental impression created using conventional dentistry techniques, or three-dimensional printing or other fabrication techniques to manufacture various interim components of dental manufacture such as dies, casts, and the like, or direct fabrication of a virtually designed restoration, such as through computerized milling of the restoration from ceramic.

In one aspect, designing the restoration may include a step of virtually adding a die spacer to a digital model. It is known in dentistry to employ a die spacer—a thin layer painted onto regions of dental models to—improve the final fit between a prepared tooth surface in a dental patient's mouth and a restoration or other dental object. The die spacer may for example provide a small void between a cast of the prepared surface and a restoration constructed for the cast which may provide a void for cement used with the final fitting, or to account for size changes in the restoration fabrication process. The die spacer may be virtually added to a digital model of a prepared surface to achieve a similar effect with a restoration that is to be directly fabricated from the digital model, or an interim component such as a fabricated cast of a dental impression used to create the restoration. Similarly, where a cast dental model is to be fabricated from a digital model, the die spacer may be added to appropriate regions of the prepared surface and any other suitable surfaces to remove or reduce the need for use of die spacers in subsequent fabrication steps. More generally, a virtual die spacer may be added to a digital model of a conventional dental model, a die, a waxup, or any other interim component of dental manufacture to account for a cementation void or other physical variations in the design of a final restoration. This cementation void or virtual die spacer may be fabricated directly into a die, waxup, or other interim component that may be three-dimensionally printed or otherwise manufactured from the digital model.

Thus in one aspect, disclosed herein is a virtual die spacer. In fabricating a dental restoration, a virtual dies spacer or cementation void may be specified, either by an originating dental office or a dental laboratory, and this void may be automatically or manually added to appropriate regions of a digital model to provide a corresponding cementation void in a final restoration. As a significant advantage, the thickness of the virtual die spacer may be explicitly specified, and may be adjusted according to, for example, a dentist's preference or according to a type of cement to be used with the restoration. Dentist preferences concerning die spacer thickness may also be stored for reuse, and dentist feedback (e.g., "too tight" or "inadequate void") may be recorded to provide sizing for a final restoration or other dental object that more closely meets and individual dentist's expectations.

In another aspect, designing the restoration may include virtually ditching a die for a restoration. In conventional dentistry, a material may be cut away from a die below the margin line (which would otherwise include bone, soft tissue, and the like) prior to use as a restoration model. This operation may be performed virtually within a user interface that includes interactive tools for manipulating a three-dimensional representation of dentition. Initially, this may include an automated, semi-automated, or manual step of defining a die in three-dimensional space by identifying a plane, a point, or a line used to separate a die from a model in an operation analogous to physically cutting a die from a conventional dental model. This may be followed by additional steps such as separate steps of explicitly identifying a margin line with a first tool and then manipulating the digital model "below" the margin line, i.e., away from the tooth surface fitted to a restoration, with a second tool to remove unwanted or unneeded areas from a volume bounded by the digital surface representation. This process may be semi-automated or automated, such as by automatic identification of the margin line and removal of a predetermined amount of sub-margin volume. The ditched die may then be directly fabricated using techniques described above.

Regardless of the interim modeling and fabrication steps, this step may result in a restoration in physical form, such as a crown, bridge, inlay, onlay, or other dental object intended for use by a dental patient.

As shown in step 508, the restoration may be scanned using, for example, an image capture system 100 such as the system described above with reference to FIG. 1, to obtain a scanned restoration.

As shown in step 510, the scanned restoration may be test fit to the digital model received in step 504, such as by virtually superimposing the scanned restoration to the digital model. This may permit evaluation of a variety of fit criteria prior to an attempt to fit the physical restoration to a prepared surface in the dental patient's mouth. This includes, for example, an evaluation of margin fit, an evaluation of void space for cement used to affix the restoration to the prepared surface, and any other evaluation relating the prepared surface directly to the restoration or abutting tooth surfaces. This may also include an evaluation of bite, occlusions, lateral excursions and any other evaluation relating to jaw motion or the mating of lower and upper arches with the restoration in place.

In another aspect, test fitting may include measuring dimensional accuracy of the scanned restoration. For example, the restoration in this context may include a prosthesis, an implant, an appliance, a restorative component, an abutment, a fixture, or any other dental object. The scanned restoration may be measured for fit between adjacent teeth, or for evaluation of contact points with teeth of an opposing arch when the restoration is fitted to a prepared surface (or more specifically, when the scanned restoration is virtually fitted to a scan of the prepared surface), or a fit to the prepared surface, possibly including an allowance for die spacing on one or more surfaces. A dentist may specify a desired tightness of fit, which may be quantified objectively (e.g., in millimeters or microns) or subjectively (e.g., loose, average, tight, etc.).

In one aspect, feedback from specific dentists may be monitored, so that subsequent restorations may more closely meet each dentist's expectations for a desired tightness of fit.

In another aspect, measuring dimensional accuracy may include evaluating a quality of margin fit between a scanned restoration and a scanned surface preparation, in order to avoid fitting difficulties at the time of fitting the physical restoration to a patient's dentition.

As shown in step 512, the test fit of step 510 may be followed by a determination of whether the physical restoration is satisfactory. If the physical restoration is not satisfactory, the process 500 may proceed to step 514 where the physical restoration is reworked, or a new restoration prepared. If the physical restoration is satisfactory, the physical model may be sent to a dental office for a final fitting procedure in the dental patient's mouth. It may also be advantageous to also forward the scan of the restoration to the originating dental office in order to begin preparation for the final fitting procedure. The process 500 may then end 518.

It will be understood that numerous variations and modifications to the above process 500 may be used. For example, although not depicted in FIG. 5, in certain instances where it appears that a physical restoration cannot be properly fabricated to fit the restoration site, e.g., the prepare surface and surrounding dentition, the dental laboratory may contact the originating dental office to request additional preparation of the target surface. All such variations and modifications are intended to fall within the scope of the methods and systems described herein.

It will further be appreciated that, even in a system where the digital surface representation is used directly to fabricate a cast dental model to which subsequent, conventional dental laboratory techniques are applied, significant advantages may be realized through elimination or mitigation of physical handling and shipping of a dental impression. Thus in one aspect, there is disclosed herein a technique for acquiring a digital model, such as a digital surface representation, of a prepared surface and/or surrounding dentition, and transmitting the digital model to a dental laboratory or rapid manufacturing facility for preparation of a restoration or other dental object.

Figure 6:
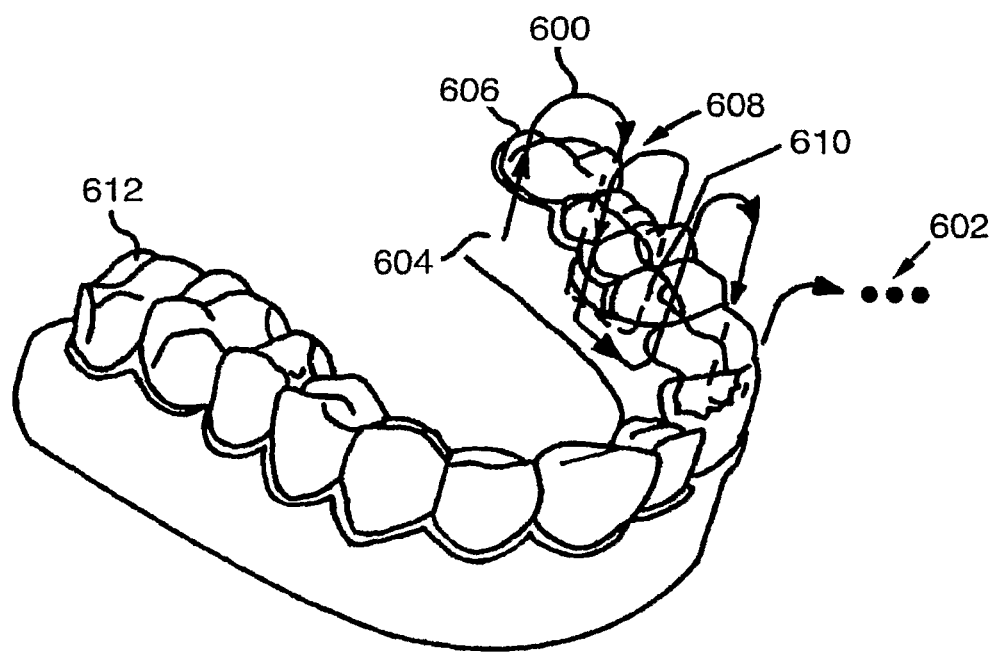
FIG. 6 illustrates a scan path that may be used with a three-dimensional image capture system.

FIG. 6 illustrates a scan path that may be used with a three-dimensional image capture system. In a system that operates to continuously acquire three-dimensional data in real time, and fits or registers incremental three-dimensional data to an aggregate three-dimensional model, it may be advantageous to scan in a manner that increases registration to the aggregate model. Thus, for example, a scan path that runs adjacent to edges of the aggregate model may provide additional registration or fit information and improve overall accuracy, particularly over large surfaces. With respect to scans of human dentition, this general approach suggests an s-shaped scan that traces from interior to exterior (or exterior to interior) surfaces of one tooth, and then reverses direction to trace an exterior-to-interior path immediately adjacent to the initial path, which may reduce overall spatial error between extremities of the arch. Without loss of generality, a more detailed example of this approach is set out below.

A scan path 600 for obtaining three-dimensional data from a dental arch 602 using a scanner such as the scanner 102 described above with reference to FIG. 1 may begin at a first lingual point 604. The scan path may then traverse laterally over an occlusal point 606 or surface of a molar to a first buccal point 608, translate to a second buccal point 610 by moving forward along the gum line, and then traverse laterally over a second occlusal point to a second lingual point. The scan path may then translate forward once again to a third lingual point, traverse laterally over a third occlusal point to a third buccal point, and once again translate forward. By scanning in this s-shaped manner, each successive pass over occlusal surfaces may be fit to data from an adjacent pass over the occlusal surfaces, as well as to one or more immediately prior frames of data. While the remainder of a scan path is not illustrated in FIG. 6, it will be understood that the scan may continue along the entire arch in this manner, finally reaching a molar 612 at the opposite extremity of the arch.

It will be understood that the spacing of adjacent passes may be greater or less than illustrated. For example, a buccal-to-lingual pass may cover a portion of a tooth, an entire tooth, or a number of teeth depending upon, for example, the field of view for data acquisition with the scanner. It will also be understood that the starting and ending points of the generally s-shaped scan are somewhat arbitrary. A scan may begin, for example at a lingual point, at an occlusal point, or at a buccal point. Further, the scan may begin at a molar, or the scan may begin at an incisor, with two consecutive scans performed from this central location to each molar extremity of the arch. All such variations are intended to fall within the scope of the scan path described herein. In general, regardless of the starting point, a generally s-shaped scan may move along adjacent buccal-to-lingual passes in the manner described above. In one aspect, real-time feedback may be provided to a user by displaying on a display a next appropriate direction of motion for a scan that follows the generally s-shaped path.

Figure 7A:
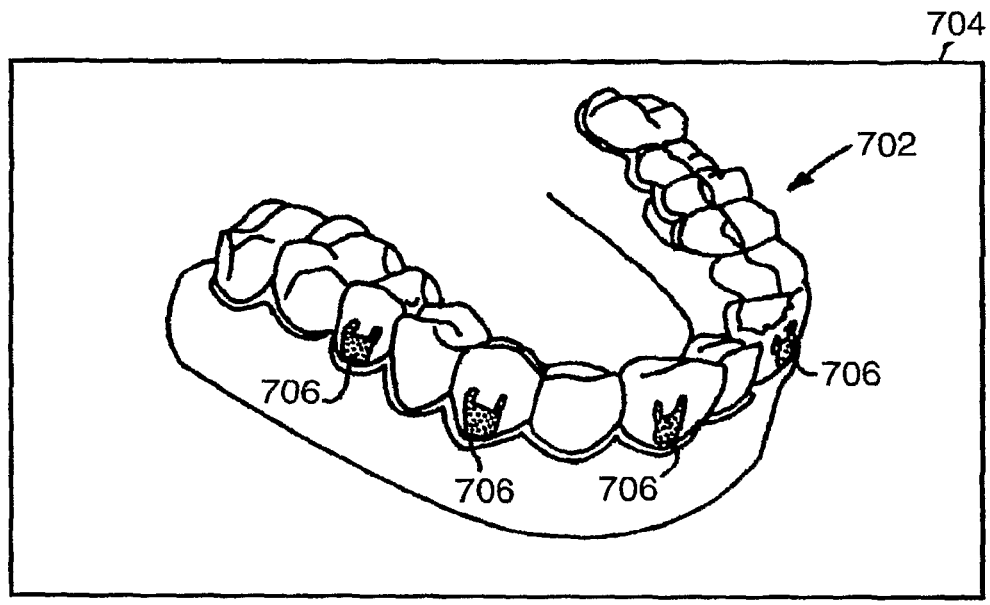
FIGS. 7A and 7B show a modeling environment for creating alignment guides for orthodontic hardware.
Figure 7B:
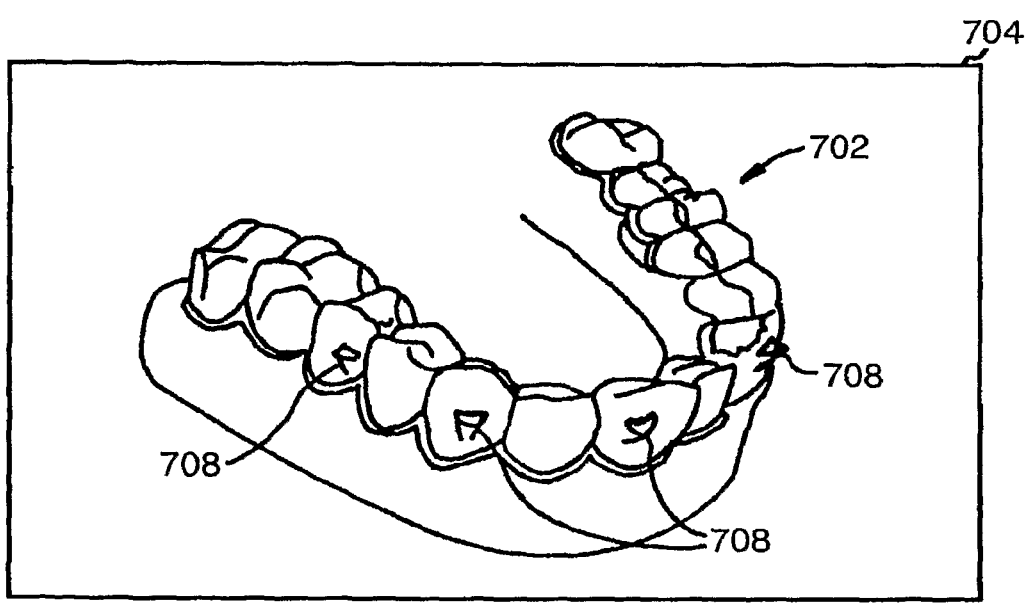

FIGS. 7A and 7B show a modeling environment for creating alignment guides for orthodontic hardware. A three-dimensional representation 702 of dentition and surrounding soft tissue may be acquired from a dental patient as described generally above, and rendered within a user interface 704 on a computer such as the image capture system 100 described above, or more generally, the client 202 described above. In various embodiments, orthodontic hardware may be virtually placed on the three-dimensional representation 702, which may be used to determine appropriate positions for one or more alignment guides, or brackets may themselves be virtually positioned on the three-dimensional representation 702 with corresponding alignment guides being generated by computer, or the alignment guides may be directly positioned on the three-dimensional representation 702. The user interface may include interactive tools for virtually positioning orthodontic hardware and/or brackets for orthodontic hardware and/or alignment guides onto the three-dimensional representation 702 within the user interface 704. The design of orthodontic hardware and any corresponding positioning of brackets or the like, may be performed by a dentist at a dental office and transmitted to a dental laboratory or other fabrication facility, or the unmodified three-dimensional representation may be transmitted to the dental laboratory along with a prescription for orthodontic hardware.

FIG. 7A shows a three-dimensional representation 702 with visual markings 706 that serve as alignment guides. This marked three-dimensional representation 702, or digital dental model, may serve as a basis for subsequent fabrication of custom orthodontic hardware. The markings 706 may be fabricated directly into a physical realization of the digital dental model, such as using pigmented printing techniques, or the markings 706 may be added to the physical realization after fabrication using additional computerized or manual marking techniques.

FIG. 7B shows a three-dimensional representation 702 with supports 708 that serve as a physical alignment guide. This three-dimensional representation 702, or digital dental model, may serve as a basis for subsequent fabrication of custom orthodontic hardware. As depicted, each support 708 may include a horizontal top surface or shelf for supporting an orthodontic fixture or other hardware. However, it will be understood that any physical form capable of supporting or engaging the intended hardware may suitable by employed, and fabricated into a physical model. The supports 708 may be fabricated directly into a physical realization of the digital dental model using techniques such as three-dimensional printing, stereo lithography, or computerized milling.

The alignment guides may serve to guide positioning of an orthodontic fixture onto the physical realization of the digital dental model to assist in fabricating custom orthodontic hardware. In an additional processing step, once the corresponding orthodontic hardware, such as brackets, is positioned onto the physical model, the position of a number of brackets may be captured in a physical template such as a foam, a vacuum-formed appliance, or the like, for direct transfer to an arch within a dental patient's mouth. The appliance may, for example, be formed of a soft, clear material for easy handling by a dentist and/or greater comfort for a dental patient. In such a process, a treating dentist may perform an additional scan of the patient's dentition immediately prior to affixing the brackets to ensure that the natural dentition still corresponds closely to the model used for virtual bracket positioning.

In another embodiment, additional modeling may be employed to create a virtual bracket carrier model—a device to carry brackets in a specific relative orientation—that can be physically realized as a bracket positioning appliance through direct fabrication using any of the techniques described above. The bracket carrier model may include one or more alignment guides for brackets such as those described generally above. Brackets may then be attached to the bracket positioning appliance for transfer to an arch within a dental patient's mouth. The treating dentist may perform an additional scan of the patient's dentition immediately prior to affixing the brackets to ensure that the natural dentition still corresponds closely to the model used to create the bracket positioning appliance.

It will be appreciated that the processes and methods disclosed herein may be realized in hardware, software, or any combination of these suitable for the three-dimensional imaging and modeling techniques described herein. This includes realization in one or more microprocessors, microcontrollers, embedded microcontrollers, programmable digital signal processors or other programmable device, along with internal and/or external memory. The may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as a camera and/or computer in a number of ways or all of the functionality may be integrated into a dedicated, standalone image capture device. All such permutations and combinations are intended to fall within the scope of the present disclosure.

It will also be appreciated that means for performing the steps associated with the processes described above may include any suitable components of the image capture system 100 described above with reference to FIG. 1, along with any software and/or hardware suitable for controlling operation of same. The user interfaces described herein may, for example, be rendered within the display 110 of the image capture system 100 of FIG. 1.

While the invention has been disclosed in connection with certain preferred embodiments, other embodiments will be recognized by those of ordinary skill in the art, and all such variations, modifications, and substitutions are intended to fall within the scope of this disclosure. Thus, the invention is to be understood with reference to the following claims, which are to be interpreted in the broadest sense allowable by law.

What is claimed is:

1. A method comprising:
seating a dental patient in a clinical office;
acquiring a digital dental impression including three-dimensional digital surface data for one or more intraoral structures from two dental arches of the dental patient, the digital dental impression including bite registration data characterizing an alignment of the two dental arches and dynamic information characterizing relative motion of the two dental arches;
transmitting the digital dental impression to a dental laboratory before the patient leaves the office, the digital dental impression including a case plan for a dental restoration, wherein the case plan specifies a cementation void for the dental restoration; and
receiving an evaluation of the case plan from the dental laboratory before the patient leaves the office based upon the bite registration data, the dynamic information, and the dynamic information, the evaluation including an identification of at least one region of the one or more intraoral structures requiring additional preparation of the one or more intraoral structures requested by the dental laboratory to prepare the dental restoration based upon the case plan.

2. The method of claim 1 further comprising preparing the one or more intraoral structures according to the evaluation.

3. The method of claim 1, wherein the evaluation includes an evaluation of surface continuity.

4. The method of claim 1, wherein the evaluation includes an evaluation of data density.

5. The method of claim 1, wherein the evaluation includes an evaluation of feature detail.

6. The method of claim 1, wherein one or more intraoral structures includes a tooth surface prepared for a dental restoration.

7. The method of claim 1, wherein the case plan includes a type of restoration.

8. The method of claim 1, wherein the case plan includes a design of restoration.

9. The method of claim 1, wherein the case plan includes a list of restoration components.

10. The method of claim 9, wherein the list of restoration components includes a full ceramic component.

11. The method of claim 9, wherein the list of restoration components includes a porcelain-fused-to-metal component.

12. The method of claim 1, wherein the case plan includes a specification of one or more restoration materials.

13. The method of claim 1 wherein the additional information requested by the dental laboratory includes a request for manual marking of a margin on the digital dental impression.

* * * * *